United States Patent [19]
Zelmanovic et al.

[11] Patent Number: 6,025,201
[45] Date of Patent: Feb. 15, 2000

[54] HIGHLY SENSITIVE, ACCURATE, AND PRECISE AUTOMATED METHOD AND DEVICE FOR IDENTIFYING AND QUANTIFYING PLATELETS AND FOR DETERMINING PLATELET ACTIVATION STATE USING WHOLE BLOOD SAMPLES

[75] Inventors: David Zelmanovic, Monsey, N.Y.; Gregory M. Colella, Upper Montclair, N.J.; Edward J. Hetherington, Brewster, N.Y.; Evelyn Sabrinah Chapman, Croton-on-Hudson, N.Y.; Lynn Paseltiner, Monroe, N.Y.

[73] Assignee: Bayer Corporation, Tarrytown, N.Y.

[21] Appl. No.: 08/884,595

[22] Filed: Jun. 27, 1997

Related U.S. Application Data

[63] Continuation-in-part of application No. 08/742,889, Nov. 1, 1996, Pat. No. 5,817,519, which is a continuation-in-part of application No. 08/581,293, Dec. 28, 1995, abandoned.

[51] Int. Cl.[7] .................................................. G01N 33/48
[52] U.S. Cl. .............................. 436/63; 436/172; 422/73; 422/82.05; 422/82.08; 356/39; 356/336; 356/337
[58] Field of Search .......................... 422/82, 73, 82.05, 422/82.08; 436/8, 10, 63, 172; 435/2; 356/39, 73, 336, 337, 338, 339, 343

[56] References Cited

U.S. PATENT DOCUMENTS

| | | |
|---|---|---|
| 3,836,849 | 9/1974 | Coulter et al. ............................. 324/71 |
| 4,202,625 | 5/1980 | Weiner et al. ............................. 356/39 |
| 4,325,706 | 4/1982 | Gershman et al. ....................... 23/230 |

(List continued on next page.)

OTHER PUBLICATIONS

S. Holme and S. Murphy, Coulter Counter and light transmission studies of platelets exposed to low temperature, ADF, EDTA and storage at 22°C. J. Lab. Clin. Med. 96, 1980, pp. 480–493.

EA Trowbridge, PM Reardon, D. Hutchinson and C. Pickering. The routine measurement of platelet volume: A comparision of light scattering and aperture impedance technologies. Clin. Phys. Physiol. Meas. 6(3), 1985, pp. 221–238.

GF Bahr and E. Zeitler. The determination of the dry mass in populations of isolated particles. Lab. Invest. 14(6), 1965, pp. 217–239.

L. Corash and B. Shafer. Use of asplenic rabbits to demonstrate that platelet age and density are related. Blood 60(1), 1982, pp. 166–171.

HHK Watson and CA Ludlam. Survival of 111–indium platelet subpopulations of varying density in normal and post–splenectomized subjects. Br. J. Hematol. 62, 1986, pp. 117–124.

JF Martin, T. Shaw, J. Heggie and DG Pennington. Measurement of the density of human platelets and its relationship to volume. Br. J. Hematol. 54, 1983, pp. 337–352.

NB Grover, J. Naaman, S. Ben–Sasson and F. Doljanski. Electrical sizing of particles in suspensions. I. Theory. Biophys. J. 9, 1969, p. 1398.

(List continued on next page.)

*Primary Examiner*—Long V. Le
*Attorney, Agent, or Firm*—Morgan & Finnegan, L.L.P.

[57] ABSTRACT

The present invention provides a highly sensitive and accurate method and system for the discrimination and quantification of platelets in a whole blood sample using automated hematology instruments. The method and system of the invention provide the accurate measurements of platelet dry mass and platelet component concentration in both normal blood samples and in abnormal blood samples, such as those from thrombocytopenic patients. The determination of platelet dry mass and platelet component concentration can serve to assess the activation state of platelets since activated platelets possess measurably lower component concentrations and refractive indices than do non-activated platelets. The method and system of the invention also allows the clinician or skilled practitioner to determine the age of a blood sample on the basis of the measured parameter of platelet component concentration.

62 Claims, 14 Drawing Sheets

U.S. PATENT DOCUMENTS

| | | | |
|---|---|---|---|
| 4,577,964 | 3/1986 | Hansen, Jr. | 356/39 |
| 4,727,020 | 2/1988 | Recktenwald | 435/6 |
| 4,735,504 | 4/1988 | Tycko | 356/336 |
| 4,778,593 | 10/1988 | Yamashita et al. | 209/3.1 |
| 4,915,501 | 4/1990 | Steen | 356/343 |
| 4,987,086 | 1/1991 | Brosnan et al. | 436/501 |
| 5,017,497 | 5/1991 | Gerard de Grooth et al. | 436/63 |
| 5,144,224 | 9/1992 | Larson | 324/71.4 |
| 5,199,576 | 4/1993 | Corio et al. | 209/564 |
| 5,284,771 | 2/1994 | Fan et al. | 436/10 |
| 5,350,695 | 9/1994 | Colella et al. | 436/63 |
| 5,360,739 | 11/1994 | Fan et al. | 436/63 |
| 5,369,037 | 11/1994 | Hansen | 436/533 |
| 5,378,633 | 1/1995 | Von Behrens et al. | 436/63 |
| 5,438,003 | 8/1995 | Colella et al. | 436/63 |
| 5,510,267 | 4/1996 | Marshall | 436/63 |
| 5,518,928 | 5/1996 | Cremins et al. | 436/40 |
| 5,540,494 | 7/1996 | Purvis, Jr. et al. | 356/73 |
| 5,559,037 | 9/1996 | Kim et al. | 436/63 |
| 5,631,730 | 5/1997 | Chupp et al. | 356/73 |

OTHER PUBLICATIONS

J. Hurley. Sizing particles with a Coulter Counter. Biophys. J. 10, 1974, p. 74.

S. Karpatkin and A. Charmatz. Heterogeneity of human platelets. I. Metabolic and Kinetic evidence suggestive of young and old platelets. J. Clin. Invest. 48, 1969, pp. 1073–1082.

GVR Born. Observations on the changes in shape of blood platelets brought about by adenosine diphosphate. J. Physiol. 209, 1070, pp. 487–511.

GVR Born, R. Dearnley, JG Faulks and DE Sharp. Quantification of the morphological reaction of platelets to aggregating agents and of its reversal of aggregation inhibitors. J. Physiol. 280, 1978, pp. 193–212.

M. Frojmovic and R. Panjwani. Geometry of normal mammalian platelets by quantitative microscopic studies. Biophys J. 16, 1976, pp. 1071–1089.

JM Paulus. Platelet size in man. Blood 46(3), 1975, pp. 321–336.

J. Zeigler, S. Murphy and FH Gardner. Microscopic platelet size and morphology in various hematologic disorders. Blood 51(3), 1978, pp. 479–486.

M. Kraytman. Platelet size in thrombocytopenias and thrombocytosis of various origin. Blood 41(4), 1973, pp. 587–597.

JD Bessman, LJ Williams and PR Gilmer. Platelet size in health and hematologic disease. Am. J. Clin. Path. 78, 1982, pp. 150–153.

J. Levin and JD Bessman. The inverse relationship between platelet volume and platelet number. J. lab. Clin. Med. 101, 1983, pp. 295–307.

JD Bessman, LJ Williams and PR Gilmer. The inverse relationship of platelet size and count in normal subjects, and an artifact of other particles. Am. J. Clin. Path. 76, 1981, pp. 289–293.

C. Giles. The platelet count and mean platelet volume. Br. J. Hematol. 48, 1981, pp. 31–37.

GA Threatte, C. Adrados, S. Ebbe and G. Brecher. Mean platelet volume: The need for a reference method. Am. J. Clin. Path. 81, 1984, pp. 769–772.

CB Thompson, DD Diaz, PG Guinn, M. Lapins, SR Kurtz and CR Valeri. The role of anticoagulation in the measurement of platelet volumes. An. J. Clin. Path. 80, 1983, pp. 327–332.

S. Murhpy and FH Gardner. Platelet storage at 22°C; Metabolic, morphologic and functional studies. J. Clin. Invest. 50, 1971, pp. 370–377.

BS Bull and MB Zucker. Changes in platelet volume produced by temperature, metabolic inhibitors, and aggregating agents. Proc. Soc. Exp. Biol. Med. 120, 1965, pp. 296–301.

JG White and W. Krivit. An ultrastructural basis for the shape changes induced in platelets by chilling. Blood 30(5), 1967, pp. 625–635.

GI Johnston, EB Pickett, RP McEver and JN George. Heterogeneity of platelet secretion in response to thrombin demonstrated by fluorescence flow cytometry. Blood 69(5), 1987, pp. 1401–1403.

JN George, EB Pickett, S. Saucerman, RP McEver, TJ Kunicki, N. Keiffer and PJ Newman. Platelet surface glycoproteins. J. Clin. Invest. 78, 1986, pp. 340–348.

DG Penington, NLY Lee, AE Roxburgh and JR McGready. Platelet density and size: The interpretation of heterogeneity. Br. J. Hematol. 34, 1976, pp. 365–376.

L. Corash, H. Tan, JR Gralnick and B. Shafer. Heterogeneity of human whole blood platelet sub–populations. I. Relationship between buoyant density, cell volume and ultrastructure. Blood 49(1), 1977, pp. 71–85.

AJ Friedhoff, JC Miller and S. Karpatkin. Heterogeniety of human platelets. VII. Platelet monoamine oxidase activity in normals and patients with autoimmune thrombocytopenic purpura and reactive thrombocytosis: Its relationship to platelet protein density. Blood 51(2), 1978, pp. 317–323.

CB Thompson, KA Eaton, SM Princiotta, CA Rushin and CR Valeri. Size dependent platelet sub–populations: Relationship of platelet volume to ultrastructure, enzymatic acitvity, and function. Br. J. Hematol. 50, 1982, pp. 509–519.

L. Corash, JL Costa, B. Shafer, JA Donlon and D. Murphy. Heterogeneity of human whole blood platelet subpopulations. III. Density–dependent differences in subcellular constituents. Blood 64(1), 1984, pp. 185–193.

CB Thompson, JA Jakubowski, PG Quinn, D. Deykin and CR Valeri. Platelet size as a determinant of platelet function. J. Lab. Clin. Med. 101, 1983, pp. 205–213.

F. Gorstein, HJ Carroll and E. Puszkin. Electrolyte concentrations, potassium flux kenetics and the metabolic dependence of potassium transport in human platelets. J. Lab. Clin. Med. 70, 1967, pp. 938–950.

S. Karpatkin. Composition of platelets. In: *Hematology*, 2nd Ed. McGraw–Hill, NY, pp. 1176–1178.

TC Bithell. Platelets and megakaryocytes. In: *Wintrobe's Clinical Hematology*, 9th Ed. vol. 1, Lea and Febiger, Philadelphia, PA, 1993, pp. 511–529.

I. Olsson, A. Dahlqvist and A. Norden. Glycogen content of leukocytes and platelets. Acta Med. Scand. 194, 1963, pp. 123–127.

P. Barkhan and MJ Silver. The lipids of human erthrocytes and platelets and their effects on thromboplastin formation. 2nd annual meeting, Amer. Soc. Hematol., St. Louis, MO, In: Blood 15, 1980, p. 428.

EE Woodside and W. Kocholaty. Carbohydrates of human and bovine platelets. Blood 16, 1960, pp. 1173–1183.

H. Braunsteiner, K. Fellinger and F. Pakesch. Structural changes in the platelets as observed by electron microscopy. Blood 9, 1954, pp. 595–601.

N. Mohandas, YR Kim, DH Tycko, J. Orlik, J. Wyatt, and W. Groner. Accurate and independent measurement of volume and hemoblobin concentration of individual red cells by laser light scattering. Blood 88(2), 1986, pp. 506–513.

GS Paterakis, NP Laoutaris, SV Alexia, PV Siourounis, AK Stamulakatou, EE Premetis, C. Sakellarious, TN Terzoglou, IG Papassotirou, and D. Loukopoulus. The effect of red cell shape on the measurement of red cell volume. A proposed method for the comparative assessment of this effect among various hematology anlaysers. Clin. Lab. Haemat. 16, 1994, pp. 235–245.

n-pentane n-hexane n-heptane

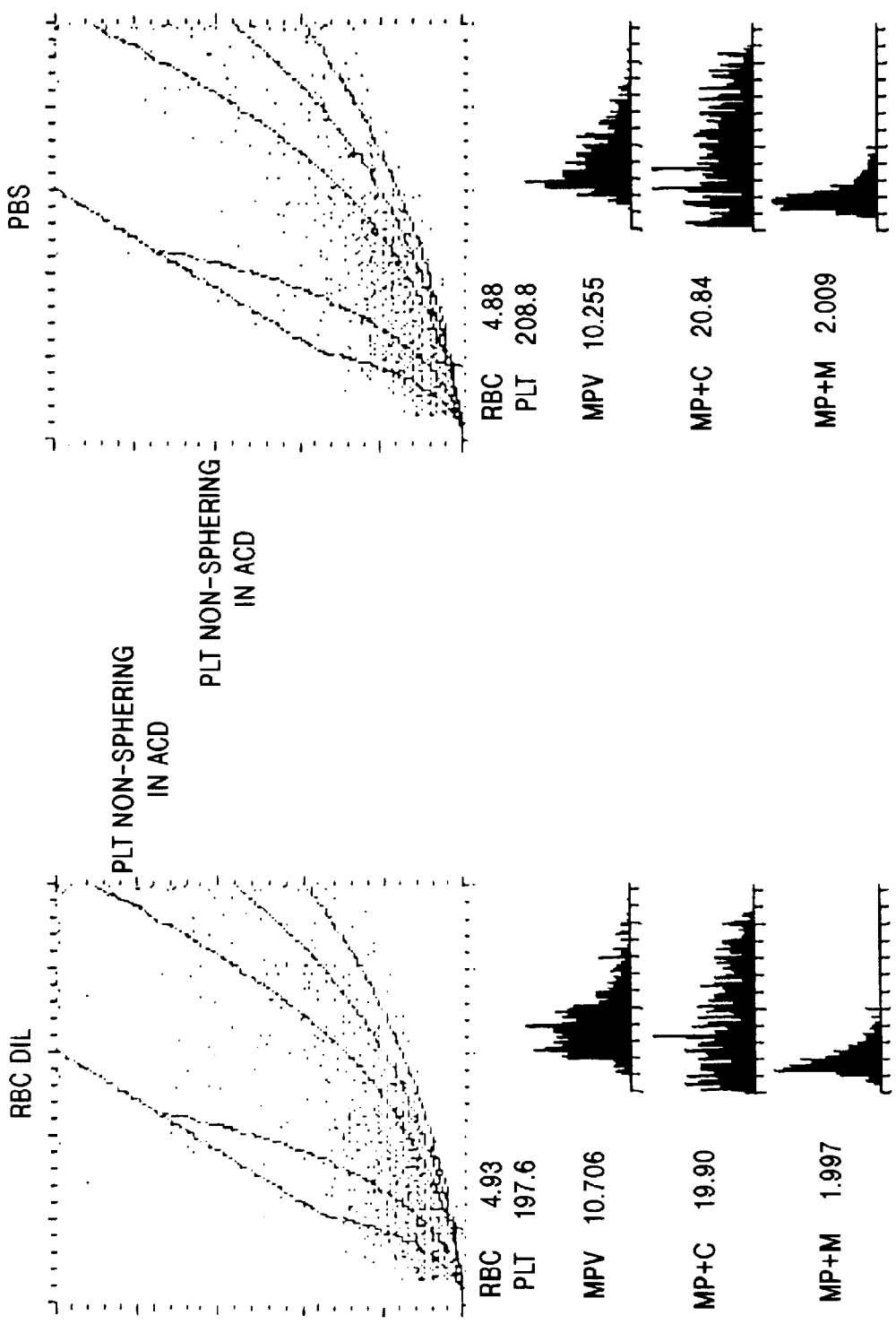

NORMAL SAMPLES : MPM : 24HR, RT vs. 1HR SAMPLES

ABNORMAL SAMPLES : MPM : 28HR, RT vs. 4HR

PLT1

PLT 27.6

MPV 8.865

H•™

PLT VOLUME
(0-20 fL)

35 X 10³/uL PLT 7.0 fL    MPV

STKS

PLT 37

MPV 7.4

□ K$_3$EDTA
o Sodium Citrate

HIGHLY SENSITIVE, ACCURATE, AND PRECISE AUTOMATED METHOD AND DEVICE FOR IDENTIFYING AND QUANTIFYING PLATELETS AND FOR DETERMINING PLATELET ACTIVATION STATE USING WHOLE BLOOD SAMPLES

This application is a continuation-in-part of application Ser. No. 08/742,889, filed on Nov. 1, 1996, now U.S. Pat. No. 5,817,519, which is a continuation-in-part of application Ser. No. 08/581,293, filed on Dec. 28, 1995, now abandoned.

FIELD OF THE INVENTION

The present invention relates to improved methods of platelet analysis and quantification using automated hematology systems. In particular, the invention relates to a high-gain method that can be used for both normal and abnormal blood samples to determine among other parameters, platelet count, platelet volume, platelet component concentration or density, and platelet dry mass with a higher degree of accuracy and precision compared with other methods.

BACKGROUND OF THE INVENTION

Although semi- and fully-automated analyzer systems are now routinely used to determine blood platelet counts, it is recognized in the art that current automated platelet determination and quantification methods are still hampered by problems of inaccuracy, lack of precision, and lack of reproducibility. This is particularly evident in the analysis of abnormal blood samples, such as those obtained from individuals or patients afflicted with a number of blood dyscrasias and thrombotic disorders such as thrombocytopenia (a decrease in the number of blood platelets), thrombocytosis, and the like. Several reasons for the difficulties and challenges in controlling accuracy of platelet counts may be attributed to 1) the large dynamic range of the platelet count and size for patients; 2) the small size of platelets; 3) the presence of interfering particles of platelet size in the samples undergoing analysis; and 4) the behavior of platelets upon in vitro aging.

Platelet analysis and quantification can be especially difficult in the case of thrombocytopenic individuals who have reduced or low numbers of platelets in their blood samples. This condition frequently results from treatments and therapies commonly used for cancer patients who have decreased thrombotic tendencies. In addition, individuals afflicted with certain immunologic diseases, particularly autoimmune disease, such as idiopathic thrombocytopenic purpura (ITP), often suffer platelet damage and destruction leading to decreased platelet numbers. Further, individuals suffering from aplastic anemia(s) also have reduced numbers of blood platelets. For example, in samples from thrombocytopenic individuals, platelet numbers are often less than $50,000/\mu l$, compared with platelet numbers in the normal range which are on the order of about $150,000-400,000/\mu l$ (J. C Dacie and S. M. Lewis, 1984, *Practical Haematology*, 6th Edition, Churchill Livingstone, London).

Indeed, the accurate enumeration of platelets became even more important with the advent of widely-available platelet replacement therapies for thrombocytopenic patients. In addition, the development and use of a variety of more sophisticated studies of platelet function, e.g., platelet activation and/or adhesiveness determinations, require accurate and precise platelet counts as an integral part of the laboratory hematology test. Also, the quality assurance of platelet packs prepared for transfusion requires that accurate platelet counting procedures be available and in place (R. K. Wertz and J. A. Koepke, 1977, *Am. J. Clin. Path.*, 68(1):195–201).

Needed in the art are more accurate, precise, and sensitive methods for the detection, discrimination, quantification, and characterization of the parameters of platelets for both normal and abnormal blood samples. In addition, accurate and precise platelet analysis methods that can be performed using whole blood samples obviate the initial preparation of platelet-rich plasma by differential centrifugation or sedimentation techniques that is required by some methods. Such whole-blood platelet analysis methods may be useful for diagnosing unsuspected platelet abnormalities, as well as for monitoring platelet counts and parameters of normal individuals and of patients at the onset of a disorder and during the course of treatment or progression of disease. In addition, methods for use on automated systems that can improve the signal resolution and the discrimination of platelets, especially in cases of low platelet counts, are needed in the art. The present invention as described provides such advantages and improvements to the art.

Two fully automated platelet counting and sizing methods are currently known and used by those in the art. One is the aperture impedance method. Whole-blood platelets in aqueous suspension are detected as they pass through a narrow aperture located between two electrodes, thereby increasing the electrical impedance in the aperture relative to that of the suspending medium in rough proportion to platelet volume. Thus, the platelet pulses provide platelet count and platelet volume. Platelets are distinguished from red blood cells in the aperture impedance method on the basis of their size, since platelets as a group are smaller than red blood cells as a group. In some applications of this method, platelet count and size determinations are refined by mathematical analysis of the shape of platelet size distributions. These distributions are fitted to log-normal curves and the parameters of the fitted curves provide platelet count and size. Although the intent of this treatment is to exclude particle debris and small red blood cells whose presence distorts the log-normal platelet volume distribution, such contaminating particles and cells are not always excluded.

A second fully automated method is the laser light scatter method. In this method, whole-blood platelets in aqueous suspension are detected as they intercept a laser beam, thus causing the incident light to scatter at characteristic angles into paths in which optical detectors are placed. The platelet signal pulses provide volume information as well as counts, since platelet volume is considered to be proportional to scattering intensity. Examples of automated flow cytometry instruments which have been designed and are employed to carry out such light scattering methods are the H•™System instruments (commercially available under the trade designation TECHNICON H•™Systems, e.g., H•™1, H•™2, H•™3, and the like, and sold by the assignee hereof) and the ORTHO ELT-8 (Ortho Diagnostics).

Another fully automated cell counting and sizing method comprises a combination of aperture impedance and light scattering. In this method, cells in aqueous suspension are detected both electrically and optically as they pass through a narrow cylindrical aperture suitable for both electrical and optical measurements. For example, this method has been demonstrated for use in cell counting, sizing and refractive index measurements of isovolumetrically sphered red blood cells (U.S. Pat. No. 5,194,909 to D. H. Tycko). The method described includes an electrical impedance detector and a single optical detector for scattered light. However, it is possible to use a plurality of optical detectors disposed at various angles with respect to the optical axis. In the method that uses an electrical impedance detector and a single optical detector, sphered red blood cells are identified and distinguished from platelets on the basis of size differences, as determined by aperture impedance measurements. The size of the red blood cells is also determined using aperture impedance. Hemoglobin concentration is determined on the basis of both the impedance values and the scattering intensities of the red blood cells.

In the ORTHO ELT-8 system, platelets are distinguished from red blood cells simply by differences in scattering intensity over a single cone angle. In the TECHNICON H•™Systems, platelets are also sized on the basis of scattering intensity over a single cone angle; however, they are distinguished from red blood cells on the basis of their characteristic scattering intensities into a pair of suitably chosen detectors. Although the platelet scattering intensity distribution is log-normal, the second laser light scattering method does not refine counts or sizing by fitting the data obtained using log-normal curves. Particle debris in this method is comprised of signals whose scattering intensities fall below a selected threshold.

As mentioned above, the aperture impedance method distinguishes platelets from red blood cells and particle debris on the basis of particle size, as well as on the basis of the log-normal distribution of platelet sizes. In cases where platelets and other particles are of overlapping size, these distinctions blur, and the best that the method can do is to recognize this failure. Moreover, the light scattering method distinguishes platelets from red blood cells based on two-dimensional boundaries, which may be crossed when red blood cells become small or if they fragment, thus also blurring the distinction between the disparate cell populations. Further, the scatter/impedance method has been demonstrated only for red blood cell analysis and not for platelet analysis.

A third, semi-automated method for platelet discrimination involves a combination of laser light scattering and fluorescence to distinguish platelets from red blood cells and particle debris. Whole-blood platelets in aqueous suspension are labelled with platelet specific-antibodies, such as CD42A. The antibodies, in turn, are bound to fluorophores such as fluorescein isothiocyanate (FITC). The labelled platelets scatter incident light and fluoresce as they pass through a fluorescence flow cytometer, such as a Becton Dickinson FACScan (Becton Dickinson). The platelets and platelet-sized particles are distinguished from red blood cells on the basis of two dimensional scattering patterns (forward scatter and side scatter). These "gated" cells are further classified on the basis of fluorescence intensity; with only platelets displaying significant fluorescence (W. Groner et al., 1994, *Blood*, No. 10 Supplement, 687a; R. Dickerhof and A. von Ruecker, 1995, *Clin. Lab. Hematol.*, 17:163–172).

Although the last two above-described methods allow the discrimination of platelets from other blood cell types and from debris, they do not provide absolute platelet counts. Furthermore, they do not determine platelet size, since there is no simple way to calibrate the methods and the systems performing the methods for this purpose. In addition, the labelling technique is labor-intensive and relatively expensive.

In addition to discriminating and quantifying platelets in blood samples, simple, inexpensive, accurate and reproducible methods for determining platelet activation (or activation state) are needed in the art. The activation state of platelets is an important parameter of platelet function as described below.

Platelet activation is a fundamental functional property of platelets, since activated platelets play an integral role in hemostasis and thrombus. When vascular injury occurs, subendothelial surfaces are exposed at the site of injury, which results in the adhesion of activated platelets to the subendothelial surface. This is followed by platelet granule release, platelet aggregation and thrombus formation. Thrombi are composed of fibrin, platelet aggregates and red blood cells.

Activated platelets are distinct from resting platelets in that the former express surface glycoproteins associated with the adhesion process. Also, activated platelets release granular components and undergo such processes as the disk-to-sphere shape change and aggregation. Swelling is also associated with the shape change.

Thrombosis is part of the normal response to vascular injury. However, increased thrombotic activity also occurs, with negative effects, in conditions such as peripheral vascular disease (D. V. Devine et al., 1993, *Arteriosclerosis and Thrombosis*, 13:857–62), cardiac ischemia (D. McTavish et al., 1990, *Drugs*, 40:238; G. DiMinno et al., 1985, *J. Clin. Invest.*, 75:328), diabetes mellitus (D. Tschoepe et al., 1991, *Seminars in Thrombosis and Hemostasis*, 17:433–438) and angina (R. C. Becker et al., 1994, *Coronary Artery Dis.*, 5:339). It is also known that blood-banked platelets in concentrates become activated during storage and, as a result, lose some of their potency (H. M. Rinder and E. L. Snyder, 1992, *Blood Cells*, 18:445). In addition, hemodialysis and surgical procedures involving extracorporeal circulation of blood are known to cause platelet activation (e.g., J. C. Reverter et al., 1994, *J. Lab. Clin. Med.*, 124:79; Y. T. Wachtfogel et al., 1993, *J. Thoracic and Cardiovascular Surg.*, 106:1–10; R. E. Scharf et al., 1992, *Arteriosclerosis and Thrombosis*, 12:1475–1487). Accordingly, the ability to identify and monitor the activation state of platelets ex vivo provides an advantageous and useful screening technique afforded by the present invention.

Platelet activation has been studied using fluorescence flow cytometry (e.g., S. J. Shattil et al., 1987, *Blood*, 70:307; C. S. Abrams et al., 1990, *Blood*, 75:128; L. Corash, 1990, *Blood Cells*, 16:97–108). Using fluorescence technology, platelets are marked with fluorescence-conjugated antibodies specific to glycoproteins that are expressed, or that undergo conformational changes, on the platelet surface as a result of platelet activation. The number of fluorescence-positive events counted on a flow cytometer represents the number of activated platelets; the fluorescence intensity per event represents the number of marked sites per cell surface. Although this technique is specific and sensitive, it is also disadvantageous in several ways, namely, it is expensive; sample preparation is time-consuming; and data analysis is not automated. Further, no standard method has been established for setting fluorescence-positive thresholds, partly because of the arbitrary nature of the threshold position and partly because of differences in experimental design.

Platelet activation has also been studied by density-gradient analysis (B. van Oost et al., 1983, *Blood*, 62:433–38). The density of platelets drops as they are activated, primarily due to swelling and secondarily due to the release of alpha- and dense-granules (S. Holme et al., 1981, *J. Lab. Clin. Med.*, 97:610–22; S. Holme et al., 1988, *J. Lab. Clin. Med.*, 112:223–231) which are denser than the platelet cytoplasm. Consequently, activated platelet samples have higher percentages of low-density platelets in density-gradient separations than do non-activated samples. The density-gradient separation technique is time consuming and requires a skilled technologist. Further, a cell counter is required to determine the number of platelets in each of the density-gradient fractions.

Accordingly, the present invention which offers a novel, inexpensive and sensitive light scattering, including light scattering/aperture impedance, technique for the determination of platelet activation provides an advancement and advantage to the art. The present method of determining platelet activation is automated and thus is efficient and time-saving for clinical use.

SUMMARY OF THE INVENTION

The present invention provides a sensitive, accurate, and precise method for the quantification and analysis of platelets in whole blood samples and is particularly useful for analyzing blood samples from individuals who have abnormal blood conditions which adversely affect the numbers and/or discrimination of blood platelets. The invention also affords a quick, simple, and inexpensive method, system, and apparatus for platelet discrimination and analysis.

It is an object of the present invention to provide an improved method of platelet analysis using automated hematology systems for gathering platelet data, including platelet count, size, component concentration and dry mass.

It is another object of the invention to provide a high-gain or high-amplification method and apparatus for platelet counting accuracy, using either at least two optical detectors or an electrical impedance detector and at least one optical detector, that offers more platelet analysis data and provides results more inexpensively and easily than previous methods employed for distinguishing non-platelets from platelets in a blood sample.

Yet another object of the invention is to provide a method of platelet counting, signal resolution, and discrimination that is sensitive and accurate for blood samples having platelet counts of from about 1,000 to less than about 50,000 platelets per microliter. In particular, the invention provides improved platelet count accuracy for thrombocytopenic samples.

Still another object of the invention is to yield cytogram results that provide well delineated and detailed depictions of particle-type distribution in the platelet-size region.

Another object of the invention is to provide a means to modify and improve current automated hematology analyzers by the addition of at least two optical channels to perform the improved method of platelet counting and analysis. The modification or improvement adds a low scattering angle/high-gain amplification channel and a high scattering angle/high-gain amplification channel to current systems plus Mie Scattering Theory-based analysis of signals to achieve the performance of the method and apparatus of the invention.

Another object of the invention is to provide a means to modify and improve current automated hematology analyzers by the addition of at least one channel to perform the improved method of platelet counting and analysis. The modification or improvement adds a scattering angle/high amplification channel plus Mie Scattering Theory-based analysis of signals to a system using aperture impedance detection methods to achieve the performance of the method and apparatus of the invention.

Another object of the invention is to allow the identification and quantification of microcytic red cells and red blood cell fragments.

Yet another object of the invention is to provide a determination of the extent of platelet activation by the measurement of platelet component concentration (MPC). In accordance with the invention, MPC values are correlated with platelet activation state.

A further object of the invention is to provide a determination of platelet dry mass which is a predictor of platelet activatability.

Another object of the invention is to provide a determination of platelet component concentration which allows the measurement of in vitro blood sample age.

Further objects and advantages afforded by the invention will be apparent from the detailed description hereinbelow.

DESCRIPTION OF THE DRAWINGS

The appended drawings of the figures are presented to further describe the invention and to assist in its understanding through clarification of its various aspects. The scatter/scatter cytograms as described hereinbelow were obtained when the present apparatus and method of the invention were employed in the determination and analysis of platelets using an electro-optical detection system of an automated hematology analyzer in accordance with the invention. In the figures presented hereinbelow, RBC=red blood cell count in $10^6/\mu l$; PLT=platelet count in $10^3/\mu l$; MPV=mean platelet volume in femtoliters (fl); MP+C is equivalent to MPC=mean platelet component concentration in g/dl; and MP+M is equivalent to MPM=mean platelet dry mass in picograms (pg).

FIG. 6A depicts a representative cytogram resulting from the analysis of ACT-anticoagulated blood samples suspended in red blood cell diluent (e.g., TECHNICON RBC Diluent). FIG. 6B depicts a representative cytogram resulting from the analysis of ACT-anticoagulated blood samples suspended in isotonic phosphate buffered saline (PBS).

FIG. 9A shows the results obtained from the TECHNICON H•™2 System using 4 hour old abnormal blood samples. In FIG. 9A, r=0.59; Syx=0.88 (Please define r and syx); slope=0.14; and intercept=4.5. FIG. 9B shows the results obtained from the TECHNICON H•™2 System using 28 hour old abnormal blood samples. In FIG. 9B, r=0.72; Syx=0.54; slope=0.13; and intercept=3.29. FIG. 9C shows the results obtained from the Coulter STKS System using 4 hour old abnormal blood samples. In FIG. 9C, r=0.13; Syx=0.95; slope=0.02; and intercept=8.06. FIG. 9D shows the results obtained from the Coulter STKS System using 28 hour old abnormal blood samples. In FIG. 9D, r=0.66; Syx=1.09; slope=0.18; and intercept=6.31.

FIG. 10A shows the results obtained from the PLT1 System using 4 hour old abnormal blood samples. In FIG. 10A, r=0.32; Syx=0.89; slope=–0.06; and intercept=10.02. FIG. 10B shows the results obtained from the PLT1 System using 28 hour old abnormal blood samples. In FIG. 10B, r=0.32; Syx=1; slope=–0.07; and intercept=11.79.

FIG. 11A shows the results obtained from the TECHNICON H•™2 System using 1 hour old normal blood samples; FIG. 11B shows the results obtained from the Coulter STKS System using 1 hour old normal blood samples; and FIG. 11C shows the results obtained from the PLT1 System of the invention using 1 hour old normal blood samples.

FIG. 12A depicts MPM accuracy data for 28 hour old abnormal samples versus 4 hour old abnormal samples stored and analyzed at room temperature. In FIG. 12A, r=0.75; Syx=0.13; slope=0.74; intercept=0.49; the 4 hour mean value is 2.04; and the 28 hour mean value is 1.99. FIG. 12B depicts MPC accuracy data for 28 hour old abnormal samples versus 4 hour old abnormal samples at room temperature. In FIG. 12B, r=0.35; Syx=1.3; slope=0.3; intercept=12; the 4 hour mean value is 22.1; and the 28 hour mean value is 18.7.

FIG. 13A represents the histogram results obtained using the PLT1 method of analysis of the invention; FIG. 13B represents the histogram results obtained using the TECHNICON H•™2 System of analysis; and FIG. 13C represents the histogram results obtained using the Coulter STKS System method of analysis.

FIGS. 14A–D demonstrate that the novel light scattering method (FIGS. 14C and 14D) of the invention and the fluorescence method (FIGS. 14A and 14B) track thrombin dose-related platelet activation in a similar manner for both sodium citrate-treated and EDTA-treated blood samples. The dose response curves for the method of the invention are presented in standard format with MPC increasing (FIG. 14C) and in "upside down" format with MPC decreasing (FIG. 14D). Both the upside down and the standard format curves display identical results, but the former orientation permits a more direct visual comparison of the results between the two methods (i.e., FIG. 14B directly compared with FIG. 14D).

DETAILED DESCRIPTION OF THE INVENTION

Figure 1:
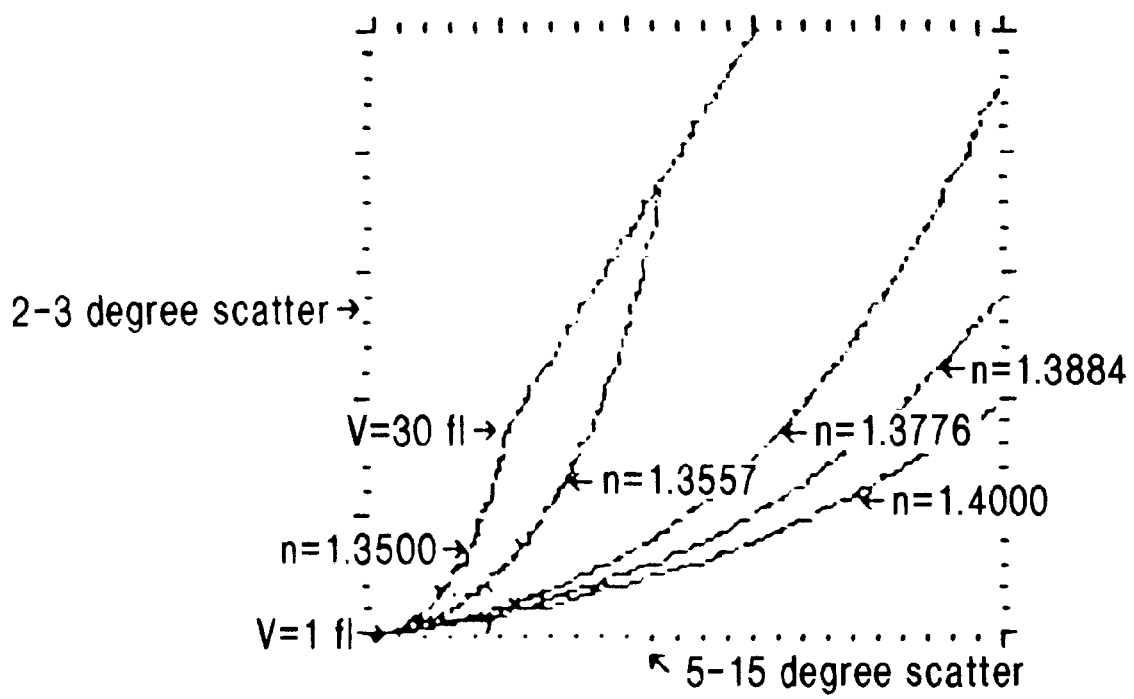
FIG. 1 depicts a platelet volume (V) versus refractive index (n) (i.e., V/n) map on a scatter/scatter cytogram. Each line shown in the cytogram represents a particular particle type as determined in the analysis and as identified in the description of FIG. 3.

The present invention provides a sensitive and accurate method of platelet quantification and characterization for use on automated hematology analyzer systems. The invention further provides an apparatus for performing the platelet quantification and characterization methods as described. As used herein, platelet is frequently abbreviated "PLT". Other abbreviations frequently used herein are the following: RBC is red blood cell; MPM is mean platelet dry mass; MPV is mean platelet volume; MPC is mean platelet component concentration; TCP is thrombocytopenic or thrombocytopenia, and TCPS is the designation used for an abnormal blood sample obtained from a patient with thrombocytopenia; MCV is mean cell volume; MCHC is mean cell hemoglobin concentration; and HCT is hematocrit.

Current types of automated hematology analyzer systems suitable for use with the scatter/scatter form of the present invention are exemplified by the H•™Systems commercially available under the trade designation TECHNICON H•™1, H•™2, H•™3, and the like, sold by the assignee hereof. For the scatter/impedance form of analysis in accordance with the present invention, platelet (or particle) detection is made electro-optically by measuring light scatter and electrically by measuring electrical impedance.

For those skilled in the art, the operating principles of the TECHNICON H•™ automated analyzer systems are set forth herein with respect to red blood cell and platelet analysis in order to clearly describe the changes made to such systems to produce the invention. In these systems, red blood cells and platelets are analyzed together in a single optical measurement channel, which includes a Helium-Neon laser light source, a flowcell, and two optical detectors. As part of its normal operating procedure, the automated system suspends two microliters (2 µl) of whole blood in 1.25 ml of TECHNICON H•™Systems RBC Diluent, a reagent solution which isovolumetrically spheres red blood cells so that they may be properly analyzed using Mie Scattering Theory, as explained herein. Red blood cell sphering reagents and diluents suitable for use in the platelet analysis method and system of the invention are described in U.S. Pat. Nos. 5,284,771, 5,360,739 and 5,411,891 to S. S.

Fan et al.; in U.S. Pat. Nos. 5,350,695 and 5,438,003 to G. Colella et al.; and in U.S. Pat. Nos. 4,575,490 and 4,412,004 to Kim and Ornstein.

A stream of approximately 10 μl of this suspension is then sheathed in a reagent fluid of matching refractive index, i.e., the TECHNICON H•™Systems RBC/Basophil surfactant sheath. The RBC/Basophil sheath is a "passive" reagent which does not interact with blood cells directly, but instead surrounds and centers the stream in the flowcell. It also provides a procession of single particles for analysis. For example, the RBC/Basophil surfactant sheath reagent composition comprises inorganic salt, such as sodium chloride, 7.7 g/l; sodium phosphate, dibasic, 2.4 g/l; sodium phosphate, monobasic, 0.3 g/l; the polyethoxylate nonionic, nonhemolytic surfactant Pluronic P-105, 1.0 g/l; an anti-oxidant reagent, such as 3,3' thiodipropionic acid, 0.10 g/l; and an antimicrobial reagent, such as Proclin 150, 0.40 g/l, at a pH of about 7.0–7.5 and an osmolality of about 285–305 mOsmol/kg.

The red blood cells and platelets in the suspension scatter some of the incident laser light as the sheathed stream of cells passes through the flow cell. The two detectors sense the light scattered at particular angular intervals relative to the axis of incidence. The detector signals are amplified so that, for normal samples, the average signals produced by red blood cells are in the middle of the range of signal amplitudes associated with red blood cells. In accordance with the invention, the light scattering intensity is measured over two cone angle intervals in two optical channels at increased first and second optical channel signal gains to produce two scattering intensity measurements sufficient to resolve the platelets from the non-platelets in the sample. The first optical channel signal value derives from an increase in the gain of the high angle detector and the second optical channel signal value derives from an increase in the gain of the low angle detector, thereby resulting in a novel high gain version of the low and high angle outputs. Also in accordance with the invention, the system displays the signals due to degree scatter of approximately 5 to 20 degrees, more preferably 7 to 15 degrees, and most preferably, 5 to 15 degrees along the X-axis of a scatter/scatter cytogram. In addition, the system displays signals due to degree scatter of approximately 1 to 7 degrees, more preferably 1 to 5 degrees, and most preferably, 2 to 3 degrees along the Y-axis of the scatter/scatter cytogram. These signals are used to determine red blood cell parameters such as volume and hemoglobin concentration, as described further herein.

Red blood cells are normally biconcave disks, whose scattering properties are sensitive to orientation as they traverse the flow cell of the above-described optical system. In order to eliminate the effects of particle orientation on signal intensity, red blood cells are sphered in the TECHNICON H•™System RBC Diluent (e.g., U.S. Pat. Nos. 4,575,490 and 4,412,004 to Kim and Ornstein). Further, Mie Scattering Theory, which provides angular scattering intensity profiles for sphered particles (such as sphered red cells), predicts that scattering intensity is sensitive to refractive index as well as to cell volume. Thus, two particles having equal volume, but having different refractive indices will have different scattering profiles. Since red blood cell refractive index depends linearly upon cellular hemoglobin concentration (R. Barer and S. Joseph, 1954, *Quarterly Journal of Microscopical Science*, 95:399–423), which varies from cell-to-cell, measurements of scattering intensity over a single cone angle interval is not likely to uniquely determine cell volume, even for sphered red blood cells. Therefore, to uniquely determine the volume of a red blood cell, it is necessary to measure its scattering intensity over at least two separate cone angle intervals. Cellular hemoglobin concentration is determined as a byproduct of the two-angle measurement.

Algorithms using Mie Theory provide the angular scattering patterns associated with particles of given volume and refractive index. Over the range of red blood cell sizes and concentrations of interest (i.e., about 30–180 fl and about 19–49 g/dl, respectively), it has been determined that a one-to-one correspondence exists between 1) the pair of scattering intensities at 2–3 degrees and 5–15 degrees, and 2) the volume and concentration of red blood cells (U.S. Pat. No. 4,735,504 to Tycko). For the TECHNICON H•™Systems, the set of correspondences is tabulated in the form of a two dimensional matrix. The indices of the matrix are comprised of the X- and Y-channel signal values and the entries of the matrix are the associated volumes and concentrations. Electromagnetic scattering theory for spherical particles (i.e., Mie Theory) has been described in detail, for example, by M. Kerker, 1969, In: *The Scattering of Light*, Academic Press.

Before automatically applying the Mie table, the system counts as blood cells all particles that exceed a pre-determined signal threshold. It then uses the two above-mentioned cone-angle measurements to designate them as either red blood cells or platelets. The two particle types occupy distinct regions of the volume/refractive index space, with red blood cells being much larger and having significantly higher refractive indices. However, the signal gains currently used in these systems provide poor discrimination of platelets from non-platelets, such as red blood cell ghosts, red cell fragments, and cellular debris. In addition, the current aperture impedance method, which relies on differences in size to distinguish platelets from other particles, does not adequately discriminate platelets from red cell fragments or debris, which have volumes similar to the volume of platelets.

By contrast, current electro-optical instruments rely on single angle-interval measurements to determine platelet volume. In the current H•™Systems, platelet volume is considered to be proportional to the 5–15 degree scattering intensity. In fact, as will be described herein, this intensity decreases with in vitro sample age due to platelet swelling (see Example 1). As a result, the reported mean platelet volume falls as the true mean platelet volume rises. Also, the single-angle method can report different volumes for platelets that actually have the same volumes, but different densities (i.e., refractive indices). Further, both electro-optical and aperture impedance instruments often under-report MPV values for thrombocytopenic samples, because low-signal debris typically comprises a significant fraction of the total particle count in these abnormal samples.

As part of the efforts of the present inventors to achieve more sensitive, accurate, and precise platelet analyses for performance on automated analyzer systems, such as, for example, the TECHNICON H•™ analyzer systems, a test station using the TECHNICON H•™1 was adapted and configured as described herein for gathering platelet data using the method and system described by the invention, which comprises increased amplification of both the X- and the Y-red blood cell optical channel signals (amplified signal gains).

The newly-configured automated system for performing the platelet discrimination analyses of the invention is referred to herein as the PLT1 system and method of the invention. For the accurate analysis of platelets, Mie Scattering Theory was used to discover the appropriate increased amplification factors as described herein. First, volume and refractive index ranges were selected for Mie analysis. The volume range selected was about 1 to 60 fl (fl=femtoliters= $10^{-15}$ liters), and preferably 1 to 30 fl. This range was selected to cover platelet sizes for all normal and most abnormal samples (J. M. Paulus, 1975, Blood, 46(3) :321–336). The refractive index range selected was about 1.340 to 1.400, preferably 1.350–1.400. The lower limit is based on the observation that platelets have higher refractive indices than their plasma media (otherwise they would be invisible) and the refractive index of plasma is typically greater than about 1.345, as determined by refractometry. The upper limit is based on the observation that most platelets are less dense (and thus, have lower refractive indices) than red blood cells, whose refractive indices rarely drop below 1.390 (cellular hemoglobin concentration of 23 g/dl). The limit was preferably extended to about 1.400 to account for the small fraction of platelets that are as dense as some red blood cells. Based on these volume and refractive index ranges and Mie Scattering Theory, the standard H•™System X-channel signals were increased or amplified about 8 to 15-fold, preferably about 12-fold, and the Y-signals were increased or amplified about 20 to 35-fold, preferably about 30-fold in accordance with the invention.

For devices operating on the scatter impedance principle, the impedance signals arising from platelets are of the same amplification as those used in the standard method of platelet counting and sizing. The platelet optical signals, if they arise from 2°–3° scattering, are amplified about 20- to 35-fold over the corresponding red blood cell signals, preferably about 30-fold. If the platelet optical signals arise from 5°–15° scattering or from 8.5°–25° scattering, they are amplified about 8- to 15-fold, preferably about 12-fold.

At these signal gain amplifications, light scattering intensities at, for example, 2 to 3 degrees, and at, for example, 5 to 15 degrees, were adequate to resolve platelets from interfering substances such as cell debris, red blood cell fragments, and red blood cell ghosts. Also, red blood cells were distinctly discerned in the method, because their signals appeared in saturation channels X=99, Y=99. Therefore, the combined scattering measurements described for the invention provide more accurate platelet counts than do current automated methods, particularly for thrombocytopenic samples, in which the fraction of interferences typically increases. Further, the scatter/scatter cytograms generated in accordance with the invention permit a visual assessment of the number, average size, and average refractive index of the platelets contained in a sample. The cytograms also provide a visual assessment of the numbers and types of other platelet-sized particles that may be present in the sample.

In addition, in another aspect of the invention, the two angle scattering measurements that are unique to the invention distinguish platelets that have released their granules (i.e., activated platelets) from those that have not, since platelets in the activated form have lower refractive indices than those in the non-activated, i.e., inactivated, form. Current automated instruments do not make this distinction.

Moreover, the high amplification allows the platelet determination system of the invention to perform Mie Scattering Theory analysis on the platelets, thereby providing platelet volume and refractive index information based on theory rather than empirical observation. In the PTL1 test station system, the five parameters measured in accordance with the invention were the red blood cell count (RBC count, $10^6/\mu l$), the platelet count (PLT count, $10^3/\mu l$), the mean platelet volume (MPV, fl), the mean platelet dry mass (MPM, pg), and the mean platelet component concentration or density (MPC, g/dl).

It is to be understood that prior to the newly-discovered method of platelet determination and its testing in the automated test system as described herein, the analytical, measured parameters of MPM and MPC were not previously available in automated platelet analysis and measurement methods and systems known and used in the art. Thus, the method and system of the invention provides an accurate and complete platelet analysis of a sample, including platelet count, mean platelet volume, mean platelet dry mass, and mean platelet component concentration. In addition, the invention also provides the sample's red blood cell count at the same time that it produces the complete platelet analysis as described further hereinbelow.

The high-amplification method of the invention was compared with other methods with respect to platelet counting and sizing accuracy, sensitivity, and qualitative and quantitative reproducibility. The other comparative methods included scattering intensity (e.g., the TECHNICON H•™2 System, Bayer Corporation, Tarrytown, N.Y.), aperture impedance (e.g., the Coulter STKS Model system, Coulter Electronics, Dade, Fla.), phase contrast microscopy, and histological blood smear estimates.

The High-Amplification System of PLT1

In accordance with an aspect of the invention, the platelet discrimination and quantification method and system of the invention employs a newly-determined high-amplification method. The measurements uniquely developed for the present invention were made on a modified TECHNICON H•™1 System, which was named the PLT1 model or paradigm system/method, due to its ability to perform unique measuring and quantification parameters on platelets and its distinction from current automated systems and devices in the art. For red blood cell analysis, the X-channel signal of the PLT1 system was amplified about 12-fold from the nominal value and the Y-channel signal was amplified about 30-fold.

Figure 2A:
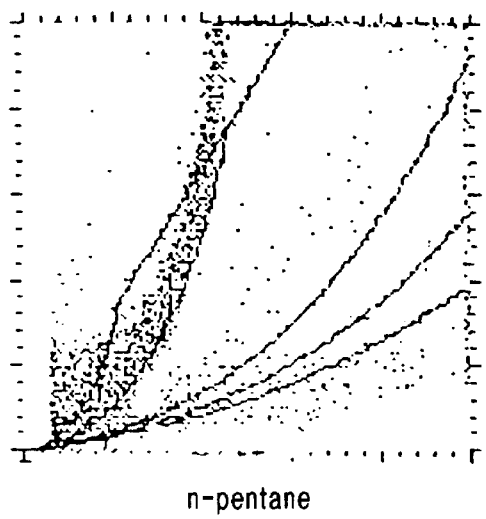
FIGS. 2A, 2B, and 2C show scatter/scatter cytograms of n-pentane, n-hexane, and n-heptane oil droplets, respectively. Each line shown in the cytogram represents a particular particle type as determined in the analysis and as identified in the description of FIG. 3.
Figure 2B:
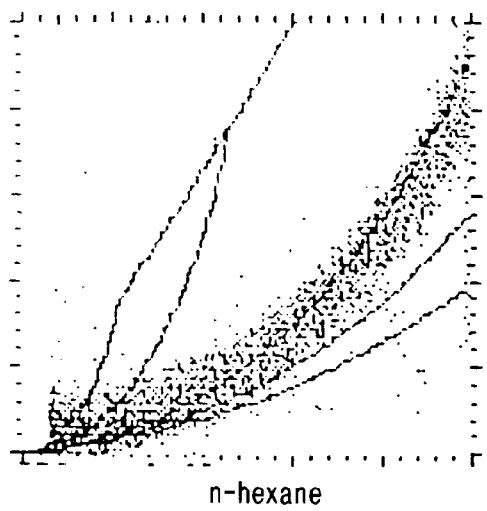
Figure 2C:
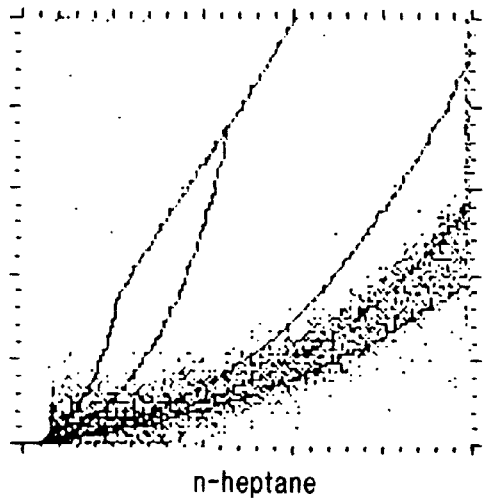

Thus, as described hereinabove and in accordance with the invention, a Mie Scattering Theory table was prepared for spheres of about 1 to 30 fl and refractive indices of about 1.350 to 1.400. The table is of the same format as that used for red blood cell analysis. The volume/refractive index (V/n) map corresponding to the table is shown in FIG. 1. X- and Y-channel gains were standardized using droplet suspensions of n-pentane (n=1.3577), n-hexane (n=1.3776) and n-heptane (n=1.3884). Fifty milliliters of each hydrocarbon was vortexed with 1 ml of RBC/Baso sheath reagent for 10 seconds and a sample was analyzed via direct cytometry, i.e., the sample was not further diluted before it passed through the flowcell. A volume/refractive index map, including table-derived curves of constant refractive index for each of the three hydrocarbons, was displayed on the report screen, along with the actual curves formed by the droplets. The signal gains were adjusted and the samples were re-run, as needed, until the actual curve for each hydrocarbon overlaid its associated table-derived curve. Examples of the patterns that were generated are displayed in FIG. 2. Thus, in accordance with the invention, platelets are specifically resolved from non-platelets by presence within a volume/refractive index map and are further resolved on the basis of the characteristic gaussian distribution of platelet refractive indices.

The RBC count performable by the PLT1 method was calibrated as on H•™ Systems with a TECHNICON Calibrator, in accordance with the manufacturer's instructions. The RBC count calibration factor, which accounts for dilution, was also applied to the platelet count (e.g., as on H•™ Systems), since the platelets and the red blood cells in a sample are subject to identical dilution factors. However, in accordance with the invention and in contrast to the comparative automated methods, no independent platelet-count calibration factor was applied in the PLT1 system and method. Therefore, differences in the platelet count between PLT1 and other technologies would not be obscured by artificial calibration factors for comparative purposes.

Figure 3:
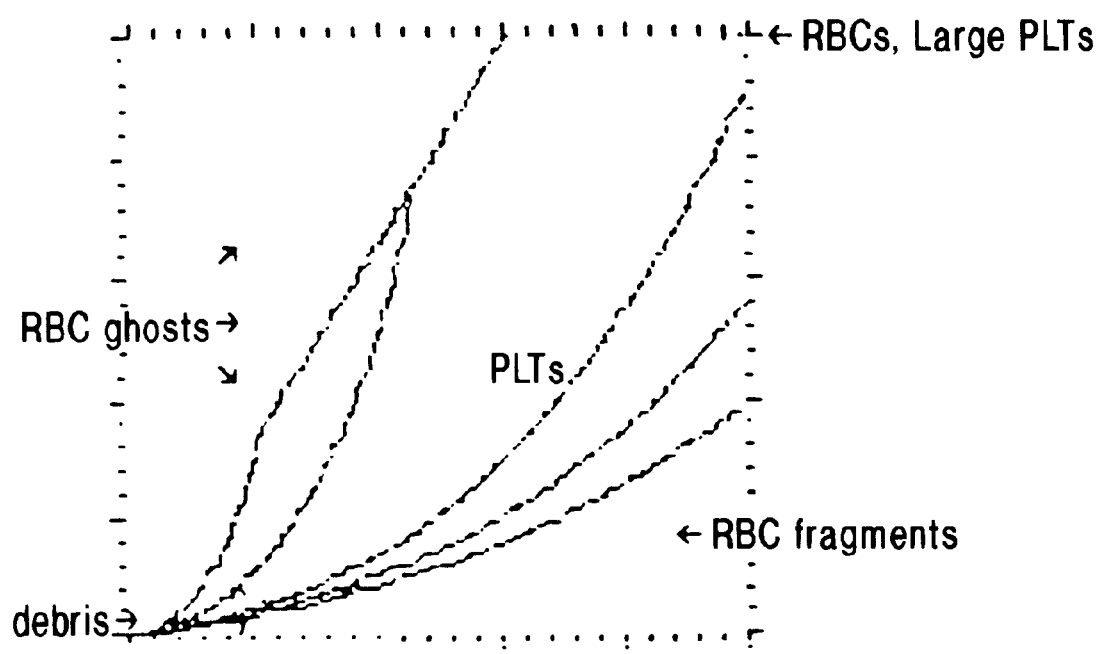
FIG. 3 demonstrates the locations of various particles, i.e., red blood cells, large platelets, red blood cell ghosts, platelets, red blood cell fragments, and origin debris in a particle-type mapping scatter/scatter cytogram. This description also applies to the cytograms shown in FIGS. 4, 5, 6, 8, and 13.

The PLT1 system is designed to process a whole blood sample by employing the hydraulics, pneumatics, chemistry, reaction time, and counting time of a RBC/PLT channel. Also, the platelet channel signals are acquired from the same pair of optical detectors that are used in the RBC/PLT channel; however, the increased signal gain amplifications acquired for measuring and determining platelets as described above are unique to the PLT1 system and are not a part of the systems and methods presently used in the art. The acquired signals for the system are analyzed as described and exemplified hereinbelow: Signals represent non-platelets (i.e., RBCs or "Others") if 1) they are outside of the V/n map (these represent "Others"); 2) they saturate the detectors (X=99, Y=99) (these represent RBCs); or 3) they are in channels X<80, Y=99 (these represent "Others"). Signals above and to the left of the map near the origin represent cellular debris. Larger signals, including those in channels X<80, Y=99 represent red cell ghosts. Saturation signals are due to RBCs and very large platelets. Signals below and to the right of the map are also due to RBC fragments (see FIG. 3).

The remaining signals on the map are analyzed as follows: First, the system computes the mean refractive index and standard deviation (SD) of signals in channels X=18 and above, using the Mie conversion table. The system excludes signals on the V/n map below channel X=18 from this part of the analysis because of possible debris contamination. Then, any particle signal having a refractive index value of between about +2 and −1.8 SD of the mean is designated as a platelet. The rest of the particle signals are designated as "Others". This yields counts for three types of particles, namely, PLTs (P), RBCs (R), and "Others" (O). The number of particles detected by the system, called $V_{sig}$, is greater than the number of particles analyzed. Therefore, P, R, and O represent the relative number of each type of particle rather than the actual raw count of each type. To obtain the raw counts, the system performs the following conversions: $N_r=(R/(R+P+O))\times V_{sig}$; $N_p=(P/(R+P+O))\times V_{sig}$; $N_o=(O/(R+P+O))\times V_{sig}$; where $N_r$=raw red blood cell count; $N_p$=raw platelet count; $N_o$=raw "other" count; and $V_{sig}$=total number of particles detected. The raw counts are then corrected for "coincidence", i.e., the simultaneous occurrence of two or more particles in the detector channel, which the detector counts as a single particle. "Others" are assumed to behave as PLTs with respect to coincidence and are therefore grouped with them in the coincidence-correction calculations. The frequency of coincidence is accurately predicted by Poisson statistics, as is appreciated by those skilled in the art. The corrected raw RBC, PLT, and "Others" counts are designated RBC', PLT' and Others'. Finally, the RBC calibration factor is applied to RBC', PLT', and Others' to yield the following values: RBC ($10^6/\mu l$); PLT ($10^3/\mu l$); and Others ($10^3/\mu l$).

It is envisioned that the volume and refractive index dynamic ranges of the improved PLT1 automated method and system can be effectively extended to handle the occasional appearance of large and dense PLTs in the saturation channels X=99, Y=99. PLT1 identifies these as red blood cells. This may be accomplished by extending the current H•™System Mie conversion table down to V<8 fl and n<1.400. The RBC/PLT Channel amplification employed in the PLT1 system provides adequate resolution of larger platelet signals for the application of extended tables to provide accurate V and n values.

The PLT1 system of the invention computes mean platelet volume (MPV, fl) and mean refractive index based on the Mie tables. The system also derives mean platelet component concentration (MPC, g/dl) and mean platelet dry mass (MPM, pg) from the means of the refractive index and the volume, as demonstrated below:

MPC (g/dl)=(mean refractive index−1.333)/(0.0018/(g/dl)), where 1.333=refractive index of water and 0.0018/(g/dl)= average refractive index (RI) increment. As will be appreciated by those in the art and as discussed further below, the RI increment value is treated as a constant in this equation to eliminate it as a variable from cell-to-cell.

MPM (pg)=MPC (g/dl)×MPV(fl)/100. (Note that g/dl=100×pg/fl.)

Figure 4:
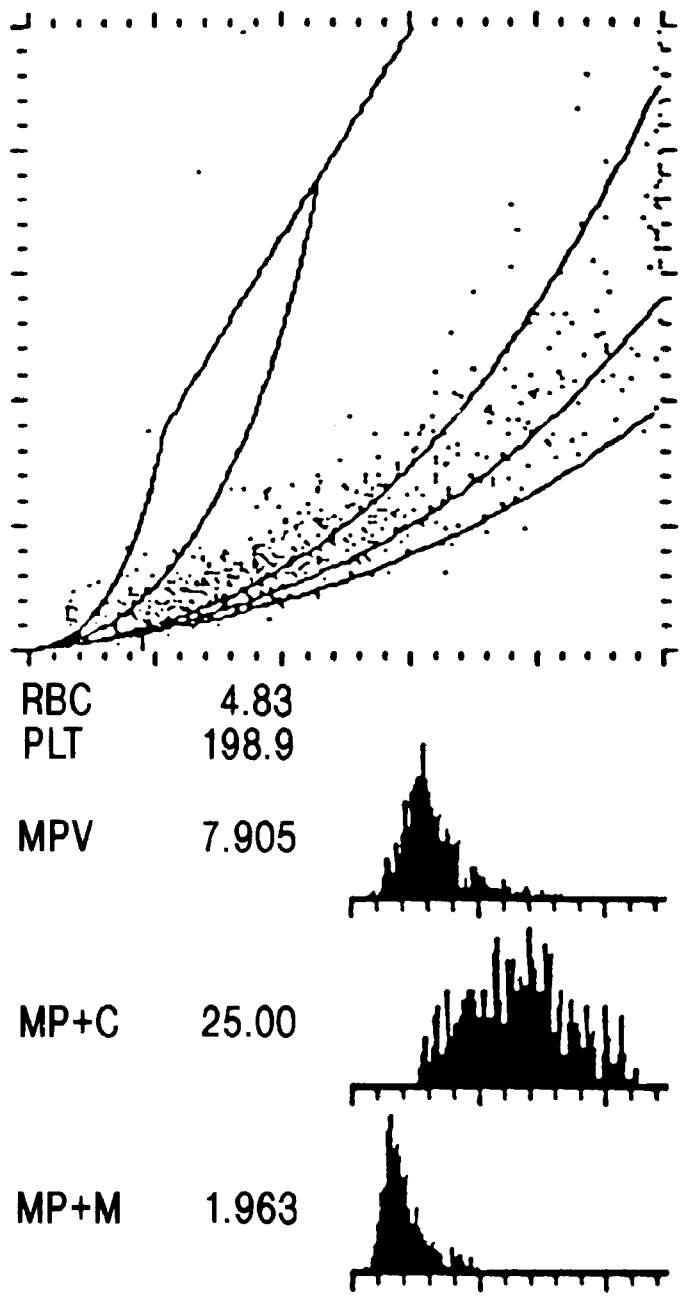
FIG. 4 depicts a representative cytogram and histograms showing a normal sample result output using the platelet determination method and system of the invention.

The average refractive index increment value is based on the fact that the major components of platelet dry mass are protein (57%), lipid (19%), and carbohydrate (8.5%) (*Wintrobe's Clinical Hematology*, Ninth Edition, 1993, page 515). The refractive index increments of these components are 0.00187/(g/dl), 0.0017/(g/dl), and 0.00143/(g/dl), respectively (S. H. Armstrong et al., 1947, *J.A.C.S.*, 69:1747–1753; R. Barer and S. Joseph, 1954, *Quarterly Journal of Microscopical Science*, 95:399–423). Using the relative concentrations of these components to assign an average refractive index increment to platelets yields a value of 0.0018/(g/dl). Of the minor components, some have higher refractive index increments and some have lower increments. The mean increment of these components is not expected to significantly change the assigned value. Note that 0.0018/(g/dl) is also the value assigned to protoplasm by the literature in the art (R. Barer and S. Joseph, 1954 *Quarterly Journal of Microscopical Science*, 95:399–423). In addition to reporting RBC and PLT counts, MPV, MPC and MPM, the system of the invention displays frequency histograms of platelet volume, platelet component concentration, and platelet dry mass (FIG. 4).

Figure 5A:
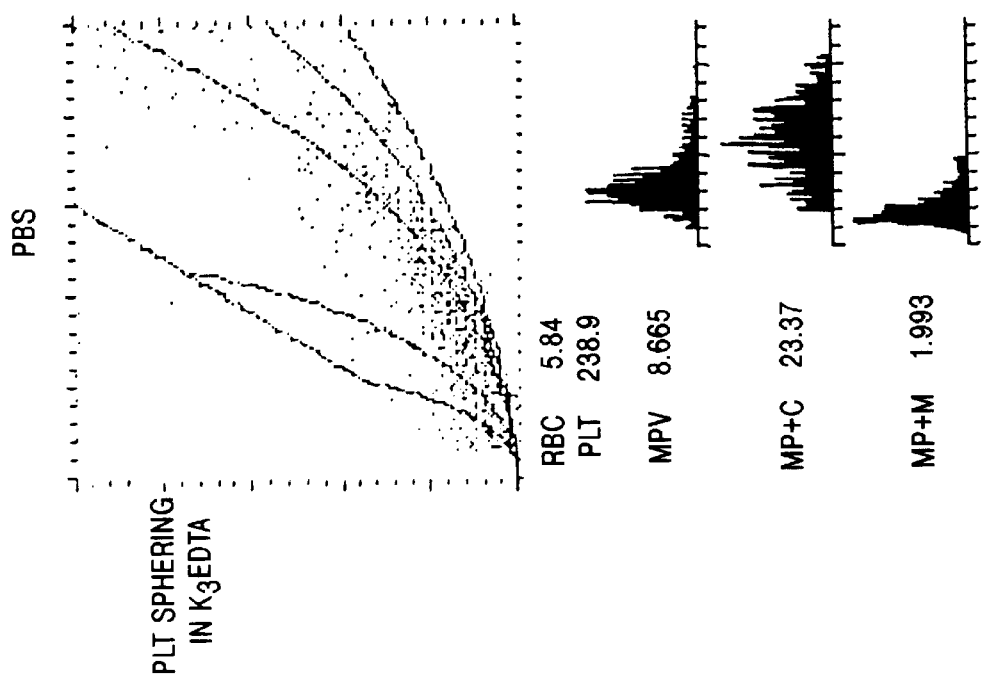
FIG. 5A depicts a representative cytogram resulting from the analysis of platelets in $K_3$EDTA-anticoagulated blood samples suspended in red blood cell diluent (e.g., TECHNICON RBC Diluent).
Figure 5B:
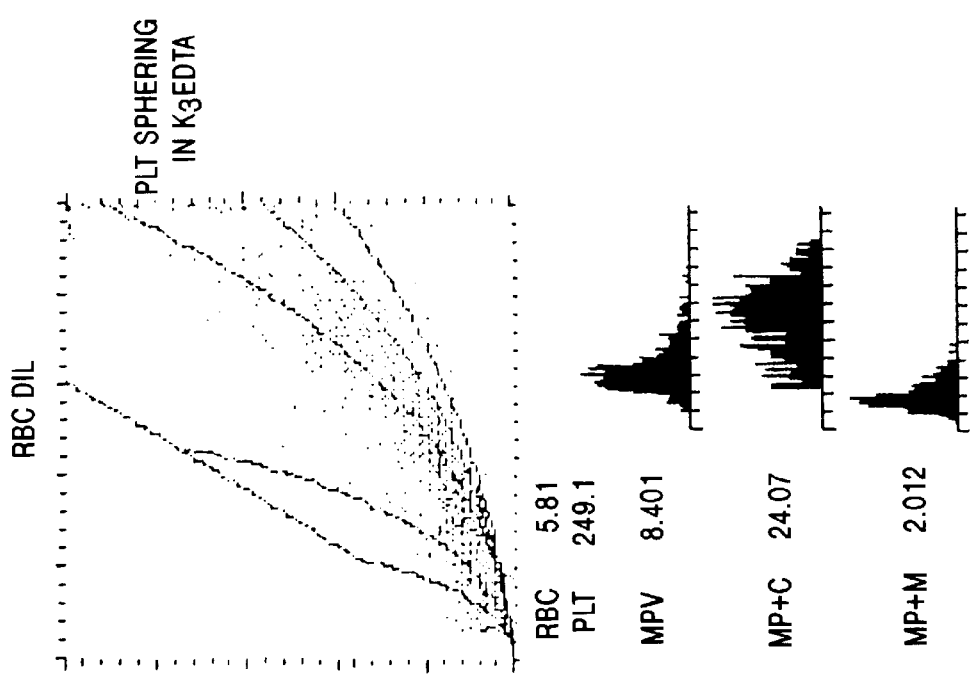
FIG. 5B depicts a representative cytogram resulting from the analysis of platelets in $K_3$EDTA-anticoagulated blood samples suspended in isotonic phosphate buffered saline (PBS). It is to be understood that samples are analyzed at room temperature, even if they have not been stored at room temperature.

The PLT1 system and method can use the same chemical reagents as the does RBC/PLT Channel method which is employed by the current TECHNICON H•™System; the sphering reagent used does not adversely affect or act upon the platelets. Moreover, additional sphering is not required for platelets that have been collected in an anticoagulant, for example, $K_3$EDTA, and analyzed in accordance with the invention. For example, FIG. 5A depicts a PLT1 scatter/ scatter cytogram generated by the PLT1 system and method of the invention for platelets that have been anticoagulated in $K_3$EDTA and then resuspended in RBC Diluent Solution. As reported in the art, $K_3$EDTA spheres platelets, albeit imperfectly (S. Holme and S. Murphy, 1980, *J. Lab. Clin. Med.*, 96:480–493, G. V. R. Born, 1970, *J. Physiol.*, 209:487–511). FIG. 5B depicts a PLT1 scatter/scatter cytogram for a second aliquot of the same sample suspended in isotonic phosphate buffered saline (PBS). As can be observed by comparing FIGS. 5A and 5B, the two cytograms resulting from the method and system of the invention have the same appearance. Moreover, the reported parameter values are also equal, within instrumental error limits. These results demonstrate that a red blood cell sphering reagent is not required for the method of the invention to provide accurate RBC counts and platelet parameter results.

In addition, FIGS. 6A and 6B show a corresponding pair of PLT1-generated scatter/scatter cytograms assessing platelets from the same donor, except that a commercially available acid/citrate/dextrose (ACT) solution was used as the anti-coagulant. In contrast to the action of $K_3$EDTA, ACT is known not to sphere platelets (S. Holme and S. Murphy, 1980, *J. Lab. Clin. Med.,* 96:480–493. G. V. R. Born, 1970, *J. Physiol.,* 209:487–511. G. V. R. Born et al., 1978, *J. Physiol.,* 280:193–212. M. Frojmovic and R. Panjwani, 1976, *Biophys. J.,* 16:1071–1089). Again, the cytograms have the same appearance, although samples suspended in ACT result in cytograms that appear more diffuse than those generated for samples suspended in $K_3$EDTA. This diffuse character is due to the random orientation of the non-spherical platelets within the flowcell and does not adversely affect the sensitivity and accuracy of the results obtained using the system and method of the invention. These results demonstrate that the red blood cell diluent does not sphere platelets; indeed, platelet sphering is not required for the accuracy of results in the invention, such that platelet analyses can be conducted on platelets that are not perfectly sphered in accordance with the present invention.

As described herein, the present invention demonstrates for the first time that sphered platelets, like red blood cells, behave "effectively" as homogeneous spheres under the chosen measurement conditions, even though platelets are not perfectly sphered and contain granules of various types, numbers, and refractive indices. Prior to the present invention, this method of analysis was thought to be effective only for sphered, homogeneous particles (see, for example, U.S. Pat. No. 4,735,504 to D. H. Tycko).

Another aspect of the invention is the application of Mie Scattering Theory to two-angle scattering measurements for platelet analysis, using the same or similar angle intervals suitable for red blood cell analysis. Prior to the present invention, those in the art were aware that the selected pair of cone angle ranges used for red blood cell analysis was specific to this cell type, since, even for red blood cells, not all angle pairs provided accurate analyses (see U.S. Pat. No. 4,735,504 to Tycko). Further, the analysis of Tycko was shown to be effective only for sphered red blood cells, which are typically about 10 times larger than platelets (i.e., MCV=85 fl for red blood cells versus MCV=8.5 fl for platelets); therefore, red blood cells provide much larger signals for analysis. Also, until the time of the invention described herein, those in the art were aware only that two angle intervals sufficed for the analysis of homogeneous and perfectly sphered particles, and it was assumed that imperfectly sphered particles required at least three angle intervals for analysis. The present invention demonstrates for the first time that the above-described parameters (i.e., pair of cone angles and two angle intervals), previously used only for red blood cell analysis are also effective for accurate and sensitive determinations and measurements of imperfectly-sphered and non-homogeneous particles, such as platelets, which have normal volume ranges of about 2–20 fl.

Current automated methods (such as those of the TECHNICON H•™ Systems and as described in U.S. Pat. No. 4,735,504 to Tycko) are designed only for the analysis of red blood cells, such as for determining red blood cell volume and cellular hemoglobin concentration. In contrast, the PLT1 method of the invention advantageously allows the simultaneous analysis of platelets and red blood cells as described and exemplified herein. In general, the PLT1 method demonstrates for the first time that an automated system, for example, the H•™ System, can be configured for simultaneous platelet and red blood cell determinations and analyses in a common optical system, in accordance with the new methodology of the invention, without sacrificing accuracy and precision of any of the determinations. The separate platelet and red blood cell Mie Theory analyses can be performed on signals collected by a single pair of optical detectors in accordance with the invention, because the platelets in a whole blood sample are analyzed under the signal amplification conditions and with the Mie Scattering Theory tables that are particularly suitable for platelet cell type in the PLT1 system and method, while the red blood cells in the sample blood sample are analyzed under amplification conditions and with Mie Scattering tables that are suitable for red blood cells.

Only the PLT1 method and system of the invention provide automated measurements of mean platelet dry mass (MPM), whether on a cell-by-cell basis or as a sample average. In principle, MPM (but not cell-by-cell dry mass or its distribution) can be determined from measurements of mean platelet component concentration, MPV and % platelet water, as follows: MPM (pg)=mean total platelet mass (pg)×(100−% water)/100, where mean total platelet mass (pg)=mean platelet density (g/ml=pg/fl)×MPV (fl). However, these determinations require both platelet density measurements (D. G. Penington et al., 1976, *Br. J. Hematol.,* 34:365–376; L. Corash et al., 1977, *Blood,* 49(1):71–85; C. B. Thompson et al., 1982, *Br. J. Hematol.,* 50:509–519; and L. Corash et al., 1984, *Blood,* 64(1):185–193) and % water measurements (F. Gorstein et al., 1967, *J. Lab. and Clin. Med.,* 70:938–950); these measurements are tedious, time-consuming, and unsuitable for high-throughput automation.

Average MPM values determined by the PLT1 system and method can be compared with indirect estimates based on established average values for platelet density, MPV, and % platelet water. It is generally agreed in the art that for platelets anti-coagulated in ACT and separated on stractan gradients, mean platelet density is approximately 1.065 g/ml (D. G. Penington et al., 1976, *Br. J. Hematol.,* 34:365–376; L. Corash et al., 1977, *Blood,* 49(1):71–85; C. B. Thompson et al., 1982, *Br. J. Hematol.,* 50:509–519; and L. Corash et al., 1984, *Blood,* 64(1):185–193) and MPV is approximately 6.5 fl (E. A. Trowbridge et al., 1985, *Clin. Phys. Physiol. Meas.,* 6(3):221–238; L. Corash et al., 1977, *Blood,* 49(1):71–85; C. B. Thompson et al., 1982, *Br. J. Hematol.,* 50:509–519). However, the art-derived MPV value is based on aperture impedance measurements made by devices calibrated with spherical polystyrene beads. Therefore, the MPV estimates for the non-spherical ACT platelets are routinely low (N. B. Grover et al., 1969, *Biophys. J.,* 9:1398; J. Hurley, 1974, *Biophys. J.,* 10:74). All other things being equal, aperture impedance measurements on $K_3$EDTA-platelets (i.e., sphered platelets) are more accurate. These types of measurements yield MPV values of approximately 8.5 fl for fresh (about 1 hour old) samples (E. A. Trowbridge et al., 1985, *Clin. Phys. Physiol. Meas.,* 6(3):221–238).

There is disagreement among those in the art as to whether or not $K_3$EDTA swells platelets in addition to sphering them (see, for example, S. Holme and S. Murphy, 1980, *J. Lab. Clin. Med.,* 96:480–493; E. A. Trowbridge et al., 1985, *Clin. Phys. Physiol. Meas.,* 6(3):221–238; G. V. R. Born, 1970, *J. Physiol.,* 209:487–511; G. V. R. Born et al., 1978, *J. Physiol.,* 280:193–212). It has been reported that density gradient measurements of $K_3$EDTA platelets yielded a mean density of 1.060 g/ml (H. H. K. Watson and C. A. Ludlam, 1986, *Br. J. Hematol.,* 62:117–124). A comparison of this value to the value of 1.065 g/ml for ACT-platelets suggests that $K_3$EDTA swells platelets by about 8%. On this basis, the MPV for "unswelled" platelets=7.8 fl (which agrees reasonably well with published values based on thrombocrit measurements (S. Karpatkin and A. Charmatz, 1969, *J. Clin. Invest.,* 48:1073–1082) and with visual microscopy (M. Frojmovic and R. Panjwani, 1976, *Biophys. J..* 16:1071–1089)). Using 7.8 to 8.5 fl as the MPV range, the mean total platelet mass range is 8.31 pg to 9.05 pg. Estimates of the % platelet water content range from 74.6% to 77% (F. Gorstein et al., 1967, *J. Lab. Clin. Med.,* 70:938–950; S. Karpatkin, "Composition of platelets", In: *Hematology.* 2nd Ed. 1977. McGraw-Hill, N.Y., pp.

1176–1178). This yields an MPM range of 1.91 pg to 2.30 pg. The mean value of 2.02 pg obtained using PLT1 is within this range. In contrast, the highest published MPM value, 2.8 pg, (S. Karpatkin, "Composition of Platelets", In: *Hematology.* 2nd Ed. 1977. McGraw-Hill, N.Y., pp. 1176–1178), is far outside this range. In addition, this value is unlikely on physical grounds, since it equates to a component concentration range of 32.9 g/dl to 35.9 g/dl, which overlaps the range of red cell component concentration—35 g/dl to 38 g/dl—for MCHC=32 g/dl to 35 g/dl (J. W. Harris and R. W. Kellermeyer, 1972, In *The Red Cell,* 2nd Ed., Harvard University Press, p. 282). Accordingly, platelets of average density should be found within the low density fraction of normal red blood cell populations. However, this is not the case, as demonstrated by common practice.

In another aspect, measurements of platelet activity, as provided by the method and system of the invention, are clinically useful. Currently, fluorescence flow cytometry (G. error of the estimate; "Xmean" is mean value for independent variable, and "Ymean" is mean value for dependent variable. Thus, even more precise MPM values for fresh samples can be obtained from aged or stored samples by extrapolation, given in vitro sample age and storage temperature. For example, given a rate of decrease 4% per 24 hours at room temperature, and an MPM of 2.00 pg at 24 hours, the MPM of the fresh sample would be 2.08 pg. It is noteworthy that the PLT1 system reports essentially the same MPM values for ACT- and for $K_3$EDTA-anticoagulated blood samples (Table 2 and FIGS. 5A and 5B). This is surprising in light of the fact that platelets are not sphered in ACT, but are sphered in $K_3$EDTA. Therefore, the PLT1 method of the invention is versatile and provides accurate and reliable MPM results for the analysis of platelets suspended in both types of anticoagulants.

TABLE 1

ACCURACY DATA

| SAMPLE | | | NORMAL DONORS: MEAN PLT DRY MASS (MPM) | | | | | NORMAL DONORS: MEAN PLT COMPONENT CONCENTRATION (MPC) | | | | | |
|---|---|---|---|---|---|---|---|---|---|---|---|---|---|
| | | | r | Syx | Xmean | Xmean-Ymean | slope | intercept | r | Syx | Xmean | Xmean-Ymean | slope | intercept |
| 8 HR, RT | vs. | 1 HR | 0.94 | 0.04 | 2.02 | 0.03 | 0.96 | 0.06 | 0.61 | 0.73 | 25.6 | 2.8 | 0.74 | 3.97 |
| 8 HR, 4 C | vs. | 1 HR | 0.94 | 0.04 | 2.02 | 0.01 | 0.97 | 0.04 | 0.45 | 0.62 | 25.6 | 1.7 | 0.41 | 13.4 |
| 24 HR, RT | vs. | 1 HR | 0.93 | 0.04 | 2.02 | 0.07 | 0.92 | 0.09 | 0.6 | 0.6 | 25.6 | 5.7 | 0.59 | 4.78 |
| 24 HR, RT | vs. | 1 HR | 0.93 | 0.05 | 2.02 | 0.03 | 1 | −0.01 | 0.37 | 1.14 | 25.6 | 3.7 | 0.6 | 6.52 |
| 8 HR, RT | vs. | 8 HR, 4 C | 0.93 | 0.04 | 2.01 | 0.02 | 0.91 | 0.16 | 0.55 | 0.77 | 23.9 | 1.1 | 0.73 | 5.35 |
| 24 HR, RT | vs. | 24 HR, 4 C | 0.91 | 0.05 | 1.99 | 0.04 | 0.84 | 0.28 | 0.42 | 0.68 | 21.9 | 2 | 0.26 | 14.19 |

I. Johnston et al., 1987, *Blood,* 69(5):1401–1403; J. N. George et al., 1986, *J. Clin. Invest.,* 78:340–348); platelet density measurement (D. G. Pennington et al., 1976, *Br. J. Hematol.,* 34:365–376; L. Corash et al. 1977, *Blood,* 49(1) :71–85; A. J. Friedhoff et al., 1978, *Blood,* 51(2):317–323; C. B. Thompson et al., 1982, *Br. J. Hematol.,* 50:509–519: L. Croash et al., 1984, *Blood,* 64(1):185–193); and MPV determination (C. B. Thompson et al., 1983, *J. Lab. Clin. Med.,* 101:205–213) are used to predict platelet activity. As mentioned hereinabove, the first of these methods, fluorescence flow cytometry, is tedious, time-consuming, and expensive. The second method, platelet density measurement, is indirect as well. The third method, MPV determination, is indirect and is affected by collection and storage conditions. Therefore, a simple, quick, inexpensive and robust method for predicting platelet activity is desirable in the art.

Potential platelet activity increases along with the number and mass of alpha- and dense-granules (L. Corash et al., 1977, *Blood,* 49(1):71–85 and L. Corash et al., 1984, *Blood,* 64(1):185–193). Since platelet dry mass correlates with granule content (Ibid.), potential platelet activity increases with MPM. Therefore, one aspect of the PLT1 method of the invention provides a simple, accurate, and inexpensive method for predicting platelet activity. Further, MPM is a robust parameter since it changes little in samples that have been stored for up to about 24 hours prior to analysis, even at room temperature. In addition, MPM behaves predictably over time, based on correlation coefficients (r) (see Table 1). Table 1 presents MPM and MPC determinations of normal blood donor samples versus time and temperature (8 hours versus 1 hour at room temperature (RT); 24 hours versus 1 hour at RT; 8 hours at RT versus 8 hours at 4° C.; and 24 hours at RT versus 24 hours at 4° C.) produced by the PLT1 system and method. In the relevant tables presented hereinbelow, "r" is correlation coefficient; "syx" is standard MPC is linearly related to platelet refractive index, which is in turn linearly related to platelet density. The results of Example 4 below, in which MPC values obtained in accordance with the methods of the invention were compared with fluorescence flow cytometric data for the dose response of normal platelets to the platelet agonist thrombin, demonstrate that MPC values correlate to PLT activation state (FIGS. 14A–14D). Significantly, the method of the invention for studying PLT activation is inexpensive, rapid and very simple to use. In addition, data analysis is easily automated. Moreover, the information that can be obtained by employing the method of the invention is essentially uniform from one instrument to another, if and when different instruments are used to carry out the method.

The method is especially suitable for the analysis of blood samples which have been anticoagulated in sodium citrate or ethylene diamine tetraacetic acid (EDTA), preferably, $K_3$EDTA. As appreciated by those in the art, solutions of sodium citrate or $K_3$EDTA can be mixed with a blood sample, or sodium citrate or $K_3$EDTA in dry form (i.e., a powder) can be dissolved in the blood sample for use as anticoagulant. As an exemplary guide, about 7 to 14 mg of $K_3$EDTA in powder form are used per 7 cc tube. Sodium citrate is used routinely as a solution at 2.0 to 5 g/dl, preferably, 3.2 to 3.8 g/dl per tube, and in a final ratio of 1 part sodium citrate to 9 parts whole blood. As is further appreciated by those in the art, $K_3$EDTA is by far the most commonly used anticoagulant for automated hematology analysis. Advantageously in this regard, the present invention provides a valuable alternative to prior methods of measuring platelets and activated platelets using antibodies, which cannot employ EDTA-containing solutions, due to the detrimental effect of such solutions on the integrity of epitopic binding sites between antibodies and the molecular structures to which they bind.

Another aspect of the invention is to provide a method and automated system to assess the relationship between MPM values and disease states and/or disease treatment regimens (see Example 2). The invention provides a convenient method of determining the effect of, for example, chemotherapy or radiation treatments on a patient's platelet granule content, by measuring MPM. Currently, it is believed that thrombocytopenia associated with peripheral destruction of platelets results in larger-than-normal platelets, while the same condition due to reduced thrombopoiesis results in normal-sized or small platelets (J. D. Bessman et al., 1982, *Am. J. Clin. Pathol.,* 78:150–153; R. B. Nelson and D. Kehl, 1981, *Cancer,* 48:954–956). Further, increased platelet size is associated with myocardial infarction (A. Eldor et al., 1982, *Br. Med. J.,* 285:397–400; H. A. Cameron et al., 1983, *Br. Med. J.,* 287:449–451; J. F. Martin et al., 1983, *Br. Med. J.,* 287:486–488). In view of the correlation between MPV and platelet dry mass (L. Corash et al., 1977, *Blood,* 49(1):71–85, and L. Corash et al., 1984, *Blood,* 64(1):185–193), one would expect a high MPM value to be associated with destructive thrombocytopenia and a low MPM value to be associated with reduced thrombopoiesis. In addition, high MPM is likely to be predictive of thrombotic potential.

TABLE 2

PLT1 SYSTEM MPM VALUES (pg)
EFFECT OF ANTI-COAGULANT
NORMAL DONORS: (1 HR SAMPLES; RT)

| DONOR # | $K_3$EDTA | ACT |
|---|---|---|
| 12 | 1.938 | 1.929 |
| 8 | 1.979 | 2.009 |
| 13 | 2.079 | 2.041 |
| 11 | 2.03 | 2.01 |
| 14 | 1.891 | 1.976 |
| 30 | 1.874 | 1.94 |
| 31 | 1.878 | 1.912 |
| 32 | 2.03 | 2.011 |
| 33 | 2.031 | 2.06 |
| 34 | 1.914 | 1.952 |
| 80 | 2.308 | 2.381 |
| 81 | 1.989 | 2.012 |
| MEAN VALUE | 1.995 | 2.019 |

In view of the description above, it will be apparent to the skilled practitioner that the present invention is also intended to encompass and is applicable, in general, to hematology analyzer instruments involving a variety of detection mechanisms and technologies that are based on light scatter as but one measured parameter, for example, light scatter/absorption, light scatter/fluorescence, light scatter/electrical impedance, light scatter/radio frequency (RF) and light scatter/light scatter technologies. Such technologies involving flow cytometry based on scattered light combined with another measured parameter for platelet determination and quantification can be referred to as "scatter/X" technologies. Illustratively, by scatter/scatter detection is meant that cell analysis is made by measuring light scatter caused by the cells at at least two different scattering angles. Other systems, such as scatter/electrical impedance or scatter/RF detection allow cell analysis to be performed by measuring light scatter at one angle and also by measuring a different known parameter, such as electrical impedance or radio frequency, respectively.

Generally, in scatter/X methods, cells in suspension pass in single-file through an optical detection system, and also, for impedance and RF measurements, through an electrical detection system. The optical system comprises a light source, usually a collimated laser beam, a narrow cylindrical tube through which the cells pass and intercept the light beam, and one or more optical detectors, such as silicon photodiodes or photomultiplier tubes, which are arranged to collect light transmitted by, scattered by, or fluoresced from the cells. The electrical system comprises an electric field, static for electrical impedance and oscillating for RF, applied across a small opening called an aperture through which the cells pass. In the scatter/impedance method, for example and as described above, the flow cell may be a cylindrical aperture suitable for both optical and electrical measurements.

In a typical scatter/impedance analysis, an aliquot of whole blood containing red blood cells, white blood cells and platelets is diluted and suspended in an isotonic medium (which is therefore electrically conductive). The dilution factor is adjusted so that cells pass in single file through the dual detection system. The impedance measurement provides cell-size information for all three cell types. The scattering measurement may provide information about cell refractive index, and therefore, cell density, for cells that behave as spheres, since the Mie Scattering Theory may be applied to the scattering signal to determine refractive index. The size and/or refractive index information is used to assign signals to the three cell types. The number of pulses of each type is used to determine the cell counts.

EXAMPLES

The following examples are illustrative of the invention. They are presented to further facilitate an understanding of the inventive concepts and in no way are to be interpreted as limiting the scope of the present invention.

EXAMPLE 1

This example describes the performance of the high-gain PLT1 channel and platelet analysis method of the invention as tested on approximately 75 normal blood samples (obtained from Bayer Corporation donors). For reference comparisons among the PLT1 method and system of the invention and systems versus methods used in the art, the blood platelet samples were analyzed using the TECHNICON H•™2 automated analyzer, the Coulter STKS analyzer, and the improved, more accurate PLT1 system. For visual reference, slides of stained blood smears were also prepared for each sample. Platelet counts, MPV values, and RBC counts were compared among the analysis modes enumerated above. Data were also collected for two parameters new to automated methodology and introduced to the art by the PLT1 system and method of the present invention, namely, Mean Platelet Dry Mass (MPM) and Mean Platelet Component Concentration (MPC).

All samples were collected into evacuated containers containing $K_3$EDTA. Samples were analyzed after 1 hour of room temperature storage, after 8 hours both at room temperature and at 4° C., and after 24 hours at room temperature and at 4° C.

To perform platelet analyses using the TECHNICON H•™2 and the Coulter STKS systems, the systems were standardized and calibrated according to the manufacturers' instructions. All samples were run and analyzed in duplicate. In addition, samples were run and analyzed in duplicate on the PLT1 test system which was standardized and calibrated as described hereinabove.

Film slides of blood smears were prepared in duplicate for all samples. Wright-Giemsa stain was then applied to the slides via the commercially available Hema-Tek 2000 Slide Stainer (Bayer Corporation). The slides were stored for platelet count and relative size reference.

The results of the normal blood analysis and PLT count comparative accuracy data are presented in Table 3; MPV comparative accuracy data are presented in Table 4; RBC count comparative accuracy data are presented in Table 5; and MPM and MPC accuracy data are presented in Table 1.

TABLE 3

NORMAL DONORS: PLT COUNT ACCURACY DATA

| | PLT1 vs. H•™2 | | | | | | PLT1 vs. COULTER STKS | | | | | |
|---|---|---|---|---|---|---|---|---|---|---|---|---|
| SAMPLE | r | Syx | Xmean | Xmean-Ymean | slope | intercept | r | Syx | Xmean | Xmean-Ymean | slope | intercept |
| 1 HR | 0.97 | 12 | 265 | −1 | 0.94 | 17 | 0.98 | 12 | 275 | 9 | 0.96 | 2 |
| 8 HR, RT | 0.96 | 15 | 261 | −7 | 0.99 | 9 | 0.97 | 15 | 273 | 5 | 0.98 | 0 |
| 8 HR, 4 C | 0.96 | 17 | 258 | −11 | 1 | 10 | 0.96 | 15 | 273 | 5 | 0.98 | 1 |
| 24 HR, RT | 0.95 | 17 | 252 | −10 | 0.98 | 15 | 0.97 | 13 | 269 | 8 | 0.96 | 3 |
| 24 HR, 4 C | 0.94 | 19 | 250 | −7 | 1.04 | −4 | 0.94 | 19 | 260 | 3 | 0.96 | 7 |

TABLE 4

NORMAL DONORS: MPV ACCURACY DATA

| | PLT1 vs. H•™2 | | | | | | PLT1 vs. COULTER STKS | | | | | |
|---|---|---|---|---|---|---|---|---|---|---|---|---|
| | r | Syx | Xmean | Xmean-Ymean | slope | intercept | r | Syx | Xmean | Xmean-Ymean | slope | intercept |
| 1 HR | 0.6 | 0.29 | 9.1 | 1.1 | 0.36 | 4.76 | 0.8 | 0.22 | 8.5 | 0.5 | 0.41 | 4.51 |
| 8 HR, RT | 0.28 | 0.43 | 8.3 | −0.6 | 0.19 | 7.31 | 0.76 | 0.29 | 8.7 | −0.2 | 0.47 | 4.76 |
| 8 HR, 4 C | 0.46 | 0.43 | 8.5 | 0 | 0.33 | 5.37 | 0.88 | 0.23 | 8.8 | 0.3 | 0.58 | 3.46 |
| 24 HR, RT | 0.43 | 0.43 | 7.2 | −3 | 0.35 | 7.62 | 0.63 | 0.37 | 9.1 | −1.1 | 0.38 | 6.73 |
| 24 HR, 4 C | 0.08 | 0.67 | 7.6 | −1.6 | −0.07 | 9.85 | 0.85 | 0.36 | 9.4 | 0.1 | 0.67 | 3.02 |

TABLE 5

NORMAL DONORS: RBC COUNT ACCURACY DATA

| | PLT1 vs. H•™2 | | | | | | PLT1 vs. COULTER STKS | | | | | |
|---|---|---|---|---|---|---|---|---|---|---|---|---|
| | r | Syx | Xmean | Xmean-Ymean | slope | intercept | r | Syx | Xmean | Xmean-Ymean | slope | intercept |
| 1 HR | 0.98 | 0.1 | 4.81 | 0.07 | 0.96 | 0.14 | 0.98 | 0.1 | 4.75 | 0.01 | 0.96 | 0.17 |
| 8 HR, RT | 0.98 | 0.09 | 4.82 | 0.08 | 0.96 | 0.13 | 0.98 | 0.1 | 475 | 0.01 | 0.93 | 0.33 |
| 8 HR, 4 C | 0.99 | 0.07 | 4.83 | 0.09 | 0.95 | 0.17 | 0.98 | 0.09 | 4.75 | 0.01 | 0.94 | 0.28 |
| 24 HR, RT | 0.99 | 0.09 | 4.83 | 0.1 | 0.94 | 0.21 | 0.98 | 0.1 | 4.75 | 0.02 | 0.94 | 0.26 |
| 24 HR, 4 C | 0.98 | 0.09 | 4.83 | 0.09 | 0.94 | 0.22 | 0.98 | 0.1 | 4.74 | 0 | 0.97 | 0.15 |

PLT counts: The platelet counts obtained from the PLT1 method of the invention agreed well with counts from the H•™2 and the STKS systems, both widely accepted platelet counting devices. It is noted that no platelet count calibration factor was applied in the PLT1 method, while the calibration factors for H•™2 and STKS were 0.85 and 1.02, respectively. This suggests that the current H•™ System Technology includes significant numbers of non-platelets in its platelet raw count.

MPV: No current method for measuring MPV is considered to be a standard in the art. Therefore, comparisons among the methods relate to the qualitative behavior of platelets. FIG. 4 shows a typical, normal sample platelet volume histogram for the PLT1 method. It represents a log-normal distribution of platelet volumes, in agreement with published results (J. M. Paulus, 1975, Blood, 46(3):321–336). Typical platelet volume distributions for the H•™2 and STKS systems are also log-normal.

For normal samples, the MPV values obtained using the PLT1 system of the invention and the comparative Coulter STKS system both indicated that MPV increases with storage time, while the values obtained using the TECHNICON H•™2 System indicated a decrease (see Table 4). This pattern for H•™2 versus STKS and PLT1 agreed with the pattern obtained using the TECHNICON H6000™ System versus the Coulter S+System as reported by Trowbridge et al. (E. A. Trowbridge et al., 1985, Clin. Phys. Physiol. Meas., 6(3):221–2382). As reported in the Trowbridge et al., paper, the TECHNICON H6000™ System (as well as in the TECHNICON H•™2 System), platelet volume is proportional to high-angle scattering intensity (5–10 degrees in H6000™ and 5–15 degrees in the H•™2 system). Mie Scattering Theory shows that scattering into these angles is sensitive to refractive index, as explained above in the Detailed Description of the Invention. As platelets age ex vivo, they swell and become less refractile due to water uptake (S. Holme and S. Murphy, 1980, J. Lab. Clin. Med., 96:480–493). This swelling reduces their high-angle scattering intensity, thereby causing the H6000™ and the H•™2 systems to report a decreased MPV when, in fact, the MPV has actually increased. However, according to measurements made by the Coulter S+ System and the Coulter STKS System and by other aperture impedance devices, platelet volume is proportional to electrical impedance. Therefore, these latter systems correctly reported increased MPV due to swelling, since impedance increases as cells swell. Because the PLT1 system of the invention converts low- and high-angle scattering signals into volumes and refractive indices using Mie Scattering Theory, as described hereinabove, the PLT1 system and method also correctly report the increased MPV due to swelling.

RBC Counts: RBC counts determined by the PLT1 system of the invention agreed well with RBC counts determined by the TECHNICON H•™2 System and the Coulter STKS System, both of which are accepted RBC counting devices.

MPM: FIG. 4 shows a typical and representative PLT1 platelet dry mass histogram and indicates that platelet dry mass is log-normally distributed within a sample. This agrees with the results of electron microscopy studies (G. F. Bahr and E. Zeitler, 1965, Lab. Invest., 14(6):217–239) and conclusions based on density gradient measurements (L. Corash and B. Shafer, 1982, Blood, 60(1):166–171). According to PLT1 system measurements, a typical MPM value for a normal sample stored for 1 hour at room temperature is 2.02 pg. This value is in excellent agreement with most of the published values, which are 2.5, 2.8, 2.06, 2.1 and 2.06 pg, respectively (G. F. Bahr and E. Zeitler, 1965, Lab. Invest., 14(6):217–2393; F. Gorstein et al., 1967, J. Lab. Clin. Med., 70:938–950; S. Karpatkin, 1977, "Composition of platelets", In: Hematology. 2nd Ed. McGraw-Hill, N.Y., pp. 1176–1178; T. C. Bithell, 1993, "Platelets and megakaryocytes", In: Wintrobe's Clinical Hematology, 9th Ed. Vol. 1. Lea and Febiger, Philadelphia, Pa., pp. 511–529; and E. E. Woodside and W. Kocholaty, 1960, Blood, 16:1173–1183). The MPM value dropped only slightly over 24 hours, i.e., by 3.5%, when samples were stored at room temperature and by 1.5% when samples were stored at 4° C. (Table 1).

MPC: FIG. 4 also shows a typical and representative PLT1 platelet component concentration histogram which is normally-distributed (i.e., displays a normal or gaussian distribution) for fresh samples. This agrees with the results of density gradient measurements (H. H. K. Watson and C. A. Ludlam, 1986, Br. J. Hematol., 62:117–124; J. F. Martin et al., 1983, Br. J. Hematol. 54:337–352). The average MPC value obtained using the PLT1 system for samples stored for 1 hour at room temperature was 25.6 g/dl. To compare this value to published values for % solids, it is necessary to determine the densities of the non-aqueous components. As described, the relative platelet composition of protein/lipid carbohydrate is 57/19/8.5 and the respective density values for these components are 1.33 g/ml, 0.93 g/ml and 1.50 g/ml, respectively (R. Barer and S. Joseph, 1954, "General Cytochemical Methods", Quarterly Journal of Microscopical Science, 95:399–423); thus, the average density of solid components is 1.26 g/ml. Therefore, the volume occupied by 25.6 g of platelet components in a dl of platelets is calculated as follows:

25.6 g×(1 ml/1.26 g)=20.3 ml or 0.203 dl. The remaining volume per dl (i.e., the water) is: 1.000 dl-0.203 dl=0.797 dl. At a density of 1 g/ml, the mass of this volume of water is 79.7 g. Therefore, % solids=(25.6/(79.7+25.6))×100= 24.3%. If $K_3$EDTA swells platelets by 8%, as described hereinabove, then, % solids=25.8%. This range of 24.3% to 25.8% is close to the range of published values, namely, 23% to 25.4% (F. Gorstein et al., 1967, J. Lab. Clin. Med., 70:938–950; S. Karpatkin, "Composition of Platelets", In: Hematology. 2nd Ed. 1977. McGraw-Hill, N.Y., pp. 1176–1178).

MPC decreased significantly over 24 hours; it decreased by 14% for samples stored at 4° C. and by 22% for samples stored at room temperature (Table 1). The statistics for MPC measured at various times and temperatures appear in Table 6. The data show that at room temperature, MPC values for samples analyzed at 1, 8, and 24 hours, respectively, do not overlap with each other, within 1.5 SD. Thus, one can determine whether a sample is 1, 8 or 24 hours old with 87% confidence by measuring its MPC. Accordingly, MPC values can be used to monitor in vitro sample age. A variety of hematologic parameters, such as MCV, MCHC, HCT and MPV, are sensitive to sample age. Consequently, false conclusions can be drawn regarding conditions such as macrocytosis, hypochromia, anemia, and platelet thrombotic potential if the effects of sample age are ignored and if accurate and reliable data are not obtained from aged samples. Therefore, monitoring sample age via MPC values using the platelet analysis and counting method and system of the invention is expected to have significant clinical value.

EXAMPLE 2

Figure 12A:
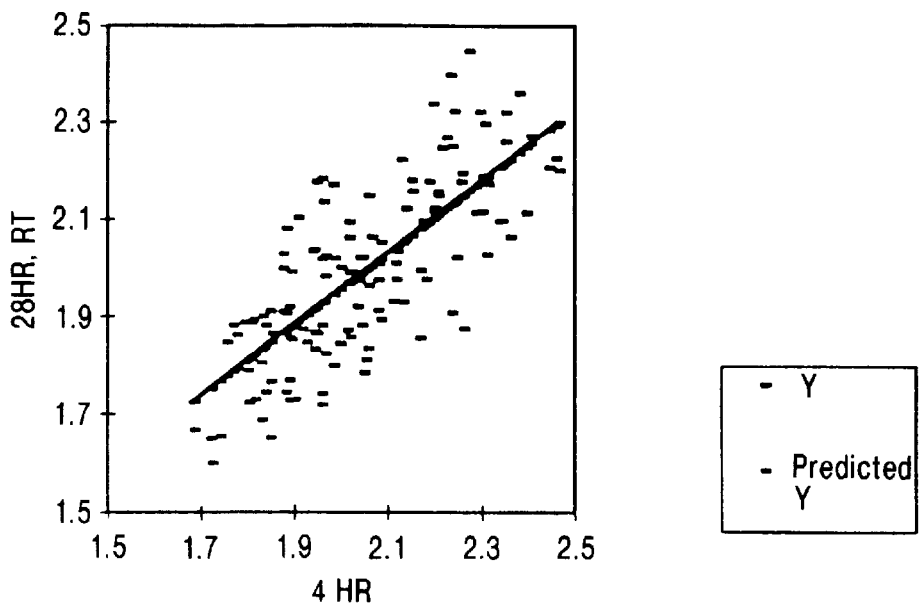
FIGS. 12A and 12B show the mean platelet dry mass (MPM) and mean platelet component concentration (MPC) accuracy data for abnormal samples using the PLT1 method and system.
Figure 12B:
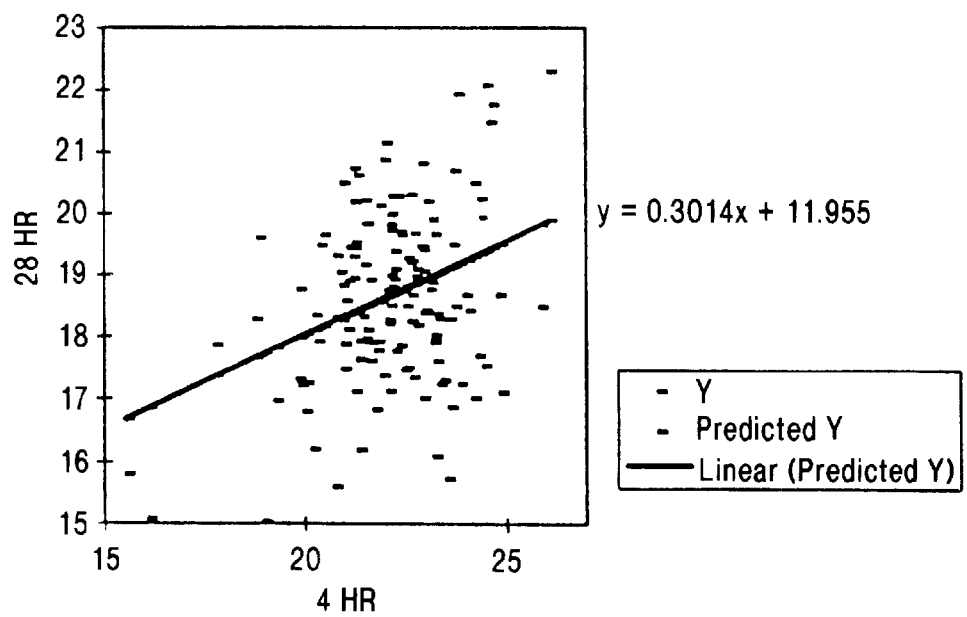

This example describes the performance of the expanded gain PLT channel (PLT1) and platelet analysis method of the invention as tested on approximately 70 abnormal blood samples (obtained from Memorial Sloan Kettering Cancer Center (MSKCC), New York). All of the samples had platelet counts below 100,000/μl and were analyzed as described in Example 1. In addition, platelet counts were determined by phase contrast microscopy, since the validity of the automated platelet counts is not well established at the present time for all thrombocytopenic samples (K. Mayer et al., 1980, Am. J. Clin. Pathol., 74:135–150; P. J. Cornbleet and S. Kessinger, 1985, Am. J. Clin. Pathol., 83:78–80). Samples were delivered to Bayer Corporation approximately 4 hours after they were collected and were analyzed at room temperature upon arrival. The samples were re-analyzed after 28 hours of storage at room temperature. The results are presented below and in Table 7 and FIG. 12.

PLT Counts: Platelet counts obtained using the PLT1 system and method of the invention agreed well with the platelet counts obtained using phase contrast microscopy for samples stored at room temperature for 4 hours. PLT1 platelet counts also agreed with TECHNICON H•™2 System counts and Coulter STKS System counts, with notable exceptions, one of which is described further in Example 3 hereinbelow.

Figure 8A:
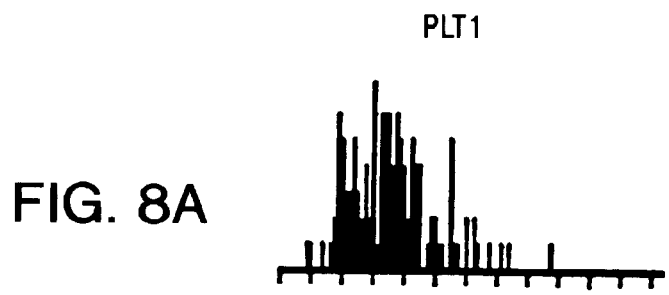
FIGS. 8A, 8B, and 8C depict platelet volume (MPV) histograms for an abnormal sample generated by several automated methods, i.e., the 1PLT1 system of the invention (FIG. 8A), the TECHNICON H•™2 System (FIG. 8B), and the Coulter STKS System (FIG. 8C).
Figure 8B:
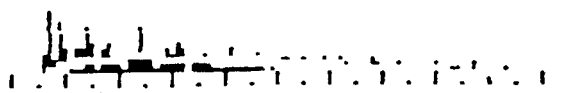
Figure 8C:
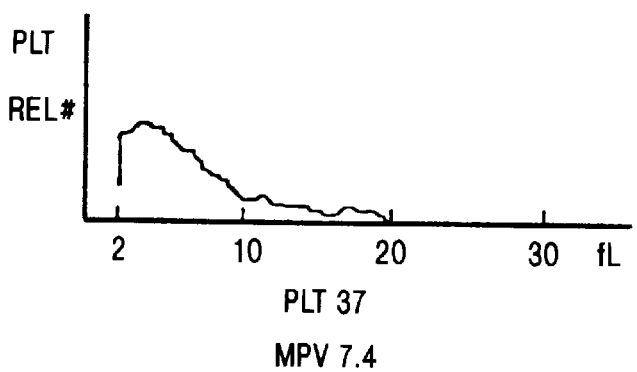
Figure 9A:
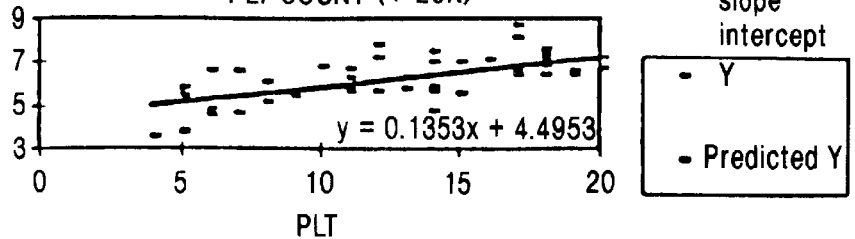
FIGS. 9A–9D depict mean platelet volume (MPV) versus abnormal platelet (PCT) count determinations (PLT count<20,000/µl) obtained using either the TECHNICON H•™2 System or the Coulter STKS System.
Figure 9B:
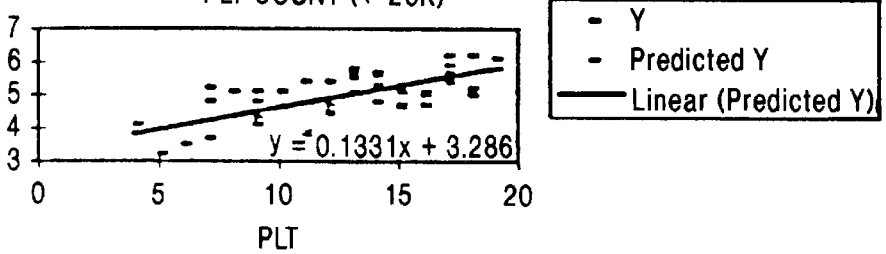
Figure 9C:
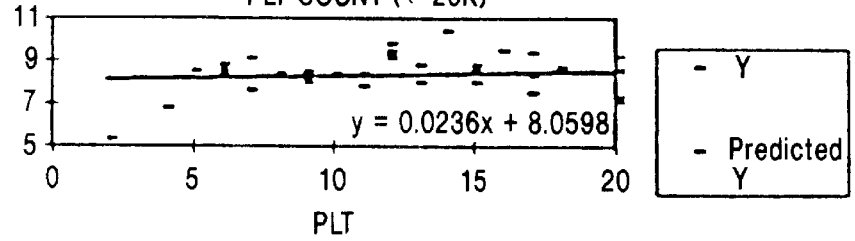
Figure 9D:
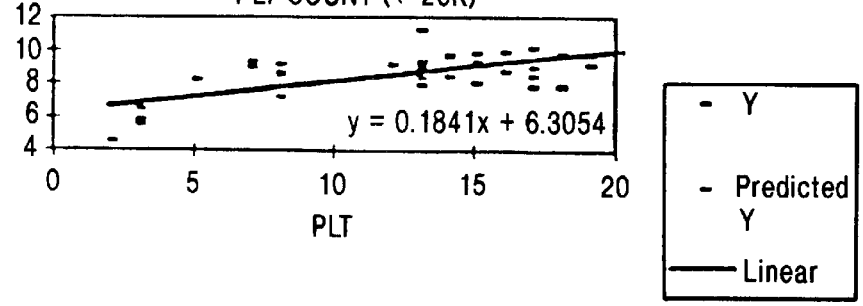
Figure 10A:
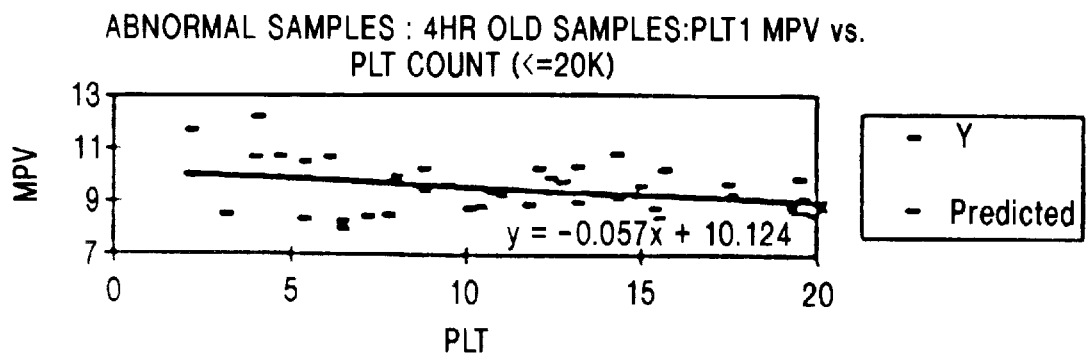
FIGS. 10A and 10B depict the mean platelet volume (MPV) versus platelet (PCT) count determination for abnormal thrombocytopenic blood samples (PLT count: <20,000/µl) obtained using the novel PLT1 System and method of the invention.
Figure 10B:
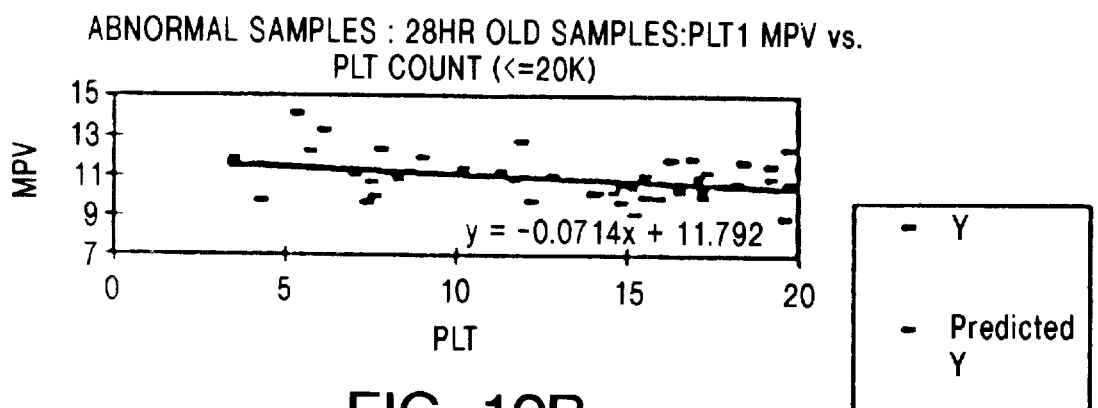
Figure 11A:
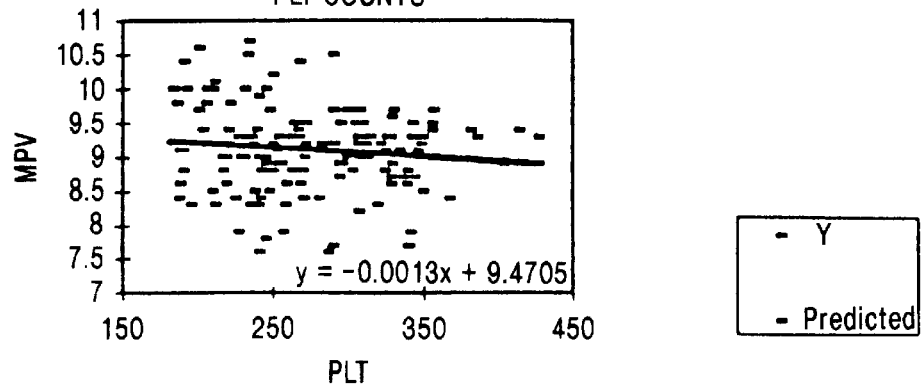
FIGS. 11A, 11B, and 11C depict mean platelet volume (MPV) versus platelet (PCT) count determinations performed on normal blood samples obtained using different automated methods, namely, the TECHNICON H•™2 System, the Coulter STKS System, and the novel PLT1 System of the invention.
Figure 11B:
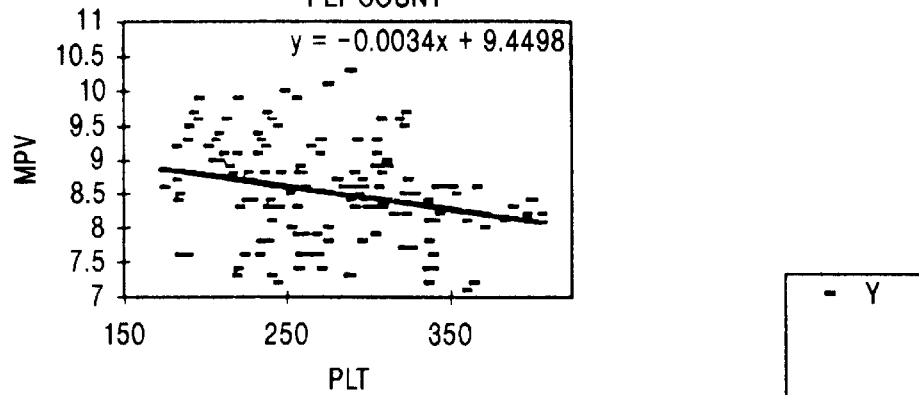
Figure 11C:
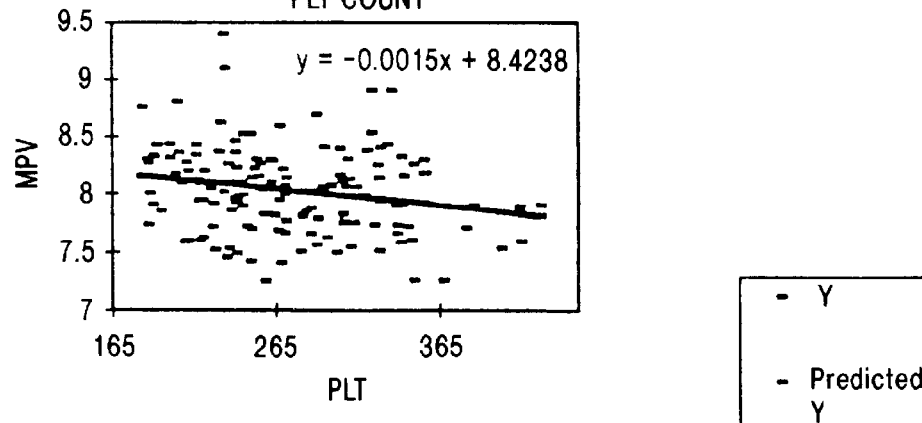

MPV: For abnormal samples, the TECHNICON h•™System and Coulter STKS System results agreed better with each other than with the results obtained using PLT1, even though the opposite was true for normal samples. The reason for this becomes clear when representative platelet volume histograms are compared. FIG. 8 shows that the platelet volume histograms generated by the TECHNICON H•™2 System and the Coulter STKS System included interfering particles in low channels. These particles distorted the log-normal platelet volume distributions and caused the systems to under-report MPV-values. In contrast, the PLT1 method of the invention excluded most of these types of interfering particles, as indicated by its log-normal platelet volume distribution. Therefore, PLT1 reported a higher MPV value than did the other systems. In addition, FIGS. 9A–9D show that, according to the H•™2 System and the Coulter STKS System measurements, MPV is directly related to PLT count (up to 20,000/μl), while FIGS. 10A and 10B show that according to PLT1 measurements, MPV and PLT count are inversely related. Moreover, according to the literature accounts, MPV and PLT counts are inversely related for normal samples and for most thrombocytopenic samples (J. D. Bessman et al., 1982, Am. J. Clin. Path., 78:150–153; J. Levin and J. D. Bessman, 1983, J. Lab. Clin. Med., 101:295–307; J. D. Bessman et al., 1981, Am. J. Clin. Path., 76:289–293; C. Giles, 1981, *Br. J. Hematol.,* 48:31–37). Thus, the literature reports are in agreement with the results generated by the PLT1 system of the invention. Also, microscopic relative-size measurements on stained blood slide films indicated that the TCP samples contained relatively more large platelets than did the normal samples. For normal samples, all three systems indicated that MPV and PLT counts were inversely related (FIG. 11), in agreement with the findings reported by those in the art.

Currently, MPV is a largely ignored parameter in platelet analysis, even though it can be used to distinguish among various hematologic disorders (J. Zeigler et al., 1978 *Blood,* 51(3):479–486; M. Kraytman, 1973, *Blood,* 41(4):587–597; J. D. Bessman et al., 1982, *Am. J. Clin. Path.,* 78:150–153; J. Levin and J. D. Bessman, 1983, *J. Lab. Clin. Med.,* 101:295–307; C. Giles, 1981, *Br. J. Hematol.,* 48:31–37. A. Eldor et al., *Br. Med. Journal,* 1982, 285:397–400. H. A. Cameron et al., *Br. Med. Journal,* 1983, 287:449–451. J. F. Martin et al., *Br. Med. Journal,* 1983, 287:486–488. G. A. Threatte, *Clin Lab Med,* 1993, 13(4):937–950). The reason for the art's disregard of MPV values is that, prior to the present invention, MPV values were considered to be unreliable. (E. A. Trowbridge et al., 1985, *Clin. Phys. Physiol. Meas.,* 6(3):221–238; G. A. Threatte et al., 1984, *Am. J. Clin. Path.,* 81:769–772) for the following possible reasons:

1) significant differences due to blood sample storage conditions are frequently obtained for MPV values between the conventional TECHNICON H•™ System and aperture impedance instruments (E. A. Trowbridge et al., 1985, *Clin. Phys. Physiol. Meas.,* 6(3):221–238. G. A. Threatte, 1993, *Clin. Lab. Med.,* 13(4):937–950, U. Lippi et al., 1987, *Am. J. Clin. Pathol.,* 87:391–393);

2) neither the conventional H•™ Systems nor the aperture impedance devices report accurate MPVs for thrombocytopenic samples, as demonstrated above; and 3) MPV is sensitive to collection and storage conditions (C. B. Thompson et al., 1983, *Am. J. Clin. Path.,* 80:327–332; S. Murphy and F. H. Gardner, 1971, *J. Clin Invest.,* 50:370–377; B. S. Full and M. B. Zucker, 1965, *Proc. Soc. Exp. Biol. Med.,* 120:296–301; J. G. White and W. Krivit, 1967, Blood, 30(5):625–635).

In contrast, the MPV results obtained using PLT1 in accordance with the present invention are valid for the following reasons:

1) the qualitative and quantitative agreement between results obtained for normal samples stored under various conditions by independent methods, namely, PLT1 and aperture impedance, places both PLT1 and aperture impedance MPV measurements on firmer ground; 2) PLT1 MPV results for thrombocytopenic samples agree qualitatively with reported literature results under a variety of conditions; and 3) PLT1 monitors the effect of sample storage on MPV by measuring MPC, as discussed hereinabove.

TABLE 6

NORMAL DONORS: MPC STATISTICS

|  | 1 HR/RT | 8 HR/RT | 24 HR/RT | 8 HR/4 C | 24 HR/4 C |
|---|---|---|---|---|---|
| Mean | 25.60899 | 22.78007 | 19.86133 | 23.91804 | 21.91432 |
| Standard Error | 0.062196 | 0.08726 | 0.070337 | 0.061206 | 0.109467 |
| Media | 25.65 | 22.87 | 19.825 | 24.03 | 22 |
| Mode | 25.75 | 22.77 | 20.13 | 24.03 | 22.58 |
| Standard Deviation | 0.730638 | 1.025071 | 0.79577 | 0.719004 | 1.223883 |
| Sample V | 0.533833 | 1.050772 | 0.633249 | 0.516966 | 1.497889 |
| Kurtosis | 0.315031 | −0.19193 | 0.33338 | −0.77856 | −0.79256 |
| Skewness | −0.06117 | −0.25711 | 0.369063 | −0.31471 | −0.16517 |
| Range | 3.82 | 5.15 | 4.01 | 3.05 | 4.98 |
| Minimum | 23.8 | 20.02 | 18.11 | 22.21 | 19.39 |
| Maximum | 27.62 | 25.17 | 22.12 | 25.26 | 24.37 |
| Sum | 3534.04 | 3143.65 | 2542.25 | 3300.69 | 2739.29 |
| Sount | 138 | 138 | 128 | 138 | 125 |
| Confidience | 0.122989 | 0.172551 | 0.139184 | 0.12103 | 0.216667 |

RBC Counts: The PLT1 system results agreed well with results obtained from both the TECHNICON H•™2 and the Coulter STKS modes of analysis. MPM: Platelet dry mass was log-normally distributed for hospital samples, and this distribution was recognizable even for samples that provided as few as 150 raw platelet signals for analysis (FIG. 8). For hospital samples stored at room temperature for 4 hours, a typical MPM value was 2.04 pg, which was effectively equal to the value obtained for normal samples stored for 1 hour at room temperature. Thus, using the PLT1 system of the invention, MPM showed the same time stability for both hospital samples and normal samples.

Figure 7A:
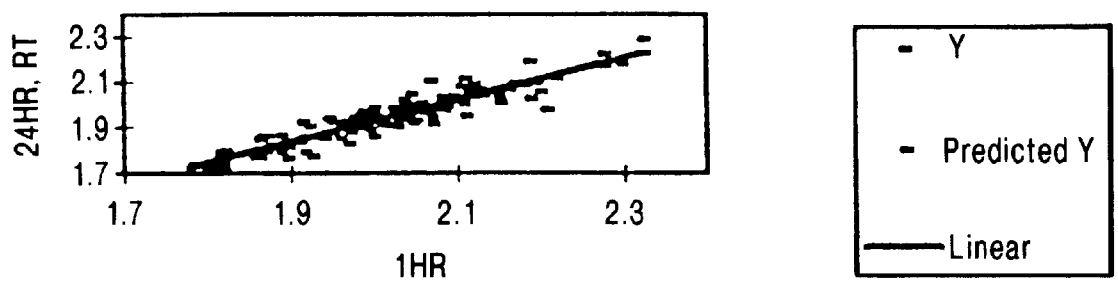
FIG. 7A is a representative graph showing mean platelet dry mass (MPM) versus time for normal blood donor samples. MPM was determined for 24 hour old normal samples versus 1 hour old normal samples stored at room temperature.
Figure 7B:
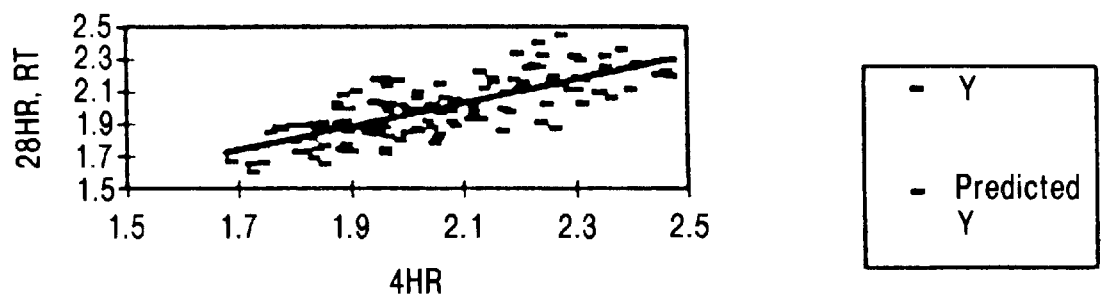
FIG. 7B shows a representative graph showing mean platelet dry mass versus time for abnormal blood donor samples. MPM was determined for 28 hour old abnormal samples versus 4 hour old abnormal samples stored at room temperature.

FIG. 7 depicts graphs which display MPM values for normal samples under various time and temperature conditions (Y axis) versus MPM for samples stored for 1 hour at room temperature (X axis). Single clusters of MPM values centered at 2 pg (the mean values for normals) are shown. FIG. 8 displays the corresponding graph for the abnormal sample set and indicates the presence of two clusters—one centered at 2.0 pg and one at 2.3 pg. The different clusters are likely to relate to differences in potential thrombotic activity. The higher MPM value for hospital samples, i.e., abnormal samples, is indicative that the platelets in these abnormal samples have more potential activity than those in normal samples. As described hereinabove, the platelet analysis method of the invention and the MPM values obtained therefrom provide a means to assess the relationship between high MPM values and disease states and/or disease treatment regimens.

MPC: Abnormal samples stored for 4 hours at room temperature had a typical MPC value of 22.1 g/dl (Table 6), which was 0.7 g/dl less than the value determined for normal samples stored for 8 hours at room temperature. MPC values obtained using PLT1 displayed the same time-dependence for hospital samples as for normal samples.

TABLE 7

| ABNORMAL SAMPLES (TCPS) METHOD | | 4 HOUR OLD SAMPLES: ACCURACY DATA | | | | | | 28 HOUR OLD SAMPLES: ACCURACY DATA | | | | | |
|---|---|---|---|---|---|---|---|---|---|---|---|---|---|
| | | r | Syx | Xmean | Xmean-Ymean | slope | intcpt. | PAR. (#) | r | Syx | Xmean | Xmean-Ymean | slope | intcpt. |
| PLT1 vs. MANUAL | PLT | 0.94 | 7.4 | 35.3 | 0.8 | 0.9 | 2.6 | | | | | | |
| H• ™2 vs. MANUAL | PLT | 0.93 | 8.2 | 35.3 | −1.4 | 0.95 | 3.1 | | | | | | |
| STKS vs. MANUAL | PLT | 0.92 | 9.2 | 35.5 | −2.4 | 1 | 2.2 | | | | | | |
| PLT1 vs. H• ™2 | PLT | 0.98 | 4.5 | 36.3 | 1.4 | 0.94 | 0.7 | PLT | 0.98 | 4 | 34.3 | 0.9 | 0.97 | 0.2 |
| PLT1 vs. STKS | PLT | 0.96 | 5.7 | 38.4 | 3 | 0.87 | 2.1 | PLT | 0.97 | 4.8 | 35.5 | 2.2 | 0.85 | 3.2 |
| H• ™2 vs. STKS | PLT | 0.97 | 5.4 | 38.3 | 1.8 | 0.9 | 2.1 | PLT | 0.96 | 5.9 | 35.5 | 1.4 | 0.85 | 3.9 |
| PLT1 vs H• ™2 | MPV | 0.3 | 1 | 7.2 | −2.4 | 0.27 | 7.6 | MPV | 0.32 | 1.2 | 5.7 | −5.6 | 0.47 | 8.6 |
| PLT1 vs. STKS | MPV | 0.66 | 0.8 | 8.9 | −0.7 | 0.54 | 4.8 | MPV | 0.42 | 1.1 | 9.1 | −2.1 | 0.37 | 7.9 |
| H• ™2 vs. STKS | MPV | 0.59 | 0.9 | 8.8 | 1.6 | 0.51 | 2.7 | MPV | 0.65 | 0.7 | 9.1 | −3.4 | 0.4 | 2.1 |
| PLT1 vs. H• ™2 | RBC | 0.99 | 0.06 | 2.94 | 0.03 | 0.97 | 0.05 | RBC | 0.99 | 0.05 | 2.96 | 0.06 | 0.97 | 0.02 |
| PLT1 vs. STKS | RBC | 0.99 | 0.06 | 2.94 | 0.03 | 1.01 | 0 | RBC | 0.99 | 0.05 | 2.94 | 0.04 | 0.96 | 0.08 |
| H• ™2 vs. STKS | RBC | 1 | 0.04 | 2.94 | 0.02 | 0.98 | 0.09 | RBC | 1 | 0.03 | 2.95 | −0.02 | 0.97 | 0.09 |

EXAMPLE 3

Figure 13A:
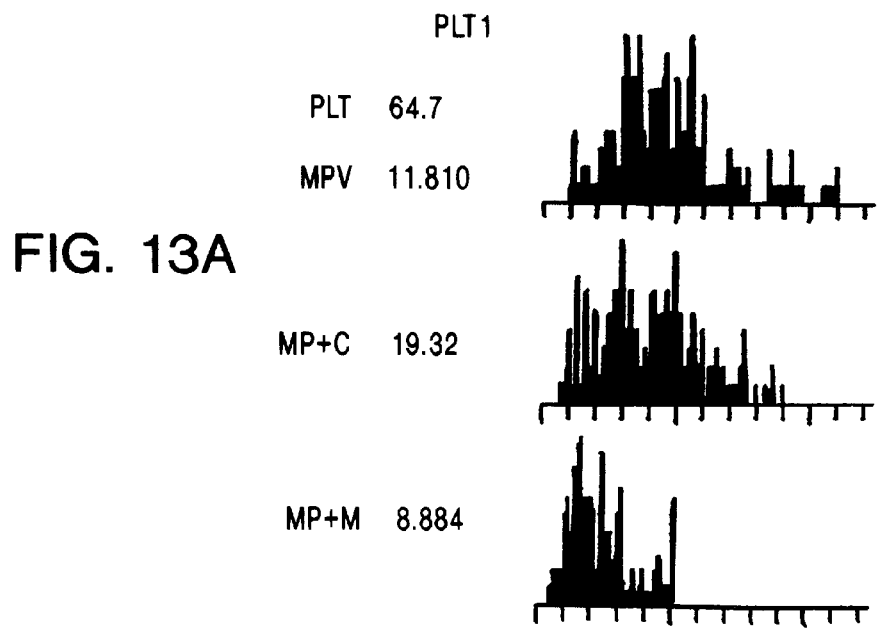
FIGS. 13A, 13B and 13C depict the platelet volume (MPV) histograms, which correspond to the results presented in Table 8 for abnormal thrombocytopenic sample #70.
Figure 13B:
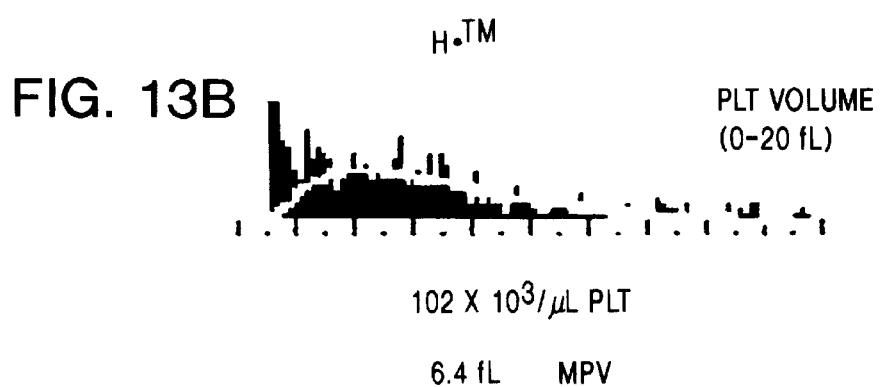
Figure 13C:
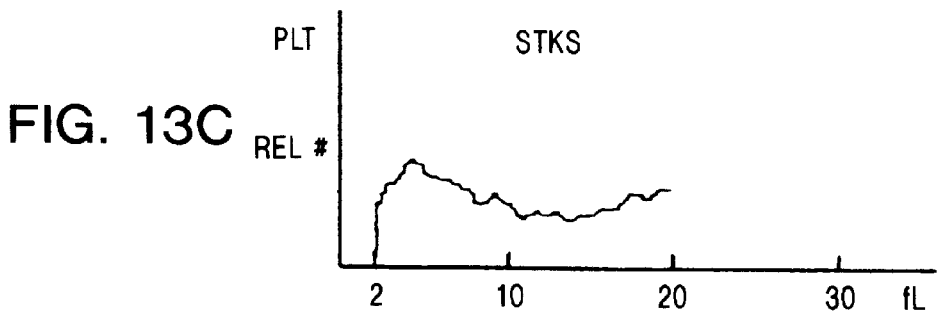
Figure 14A:
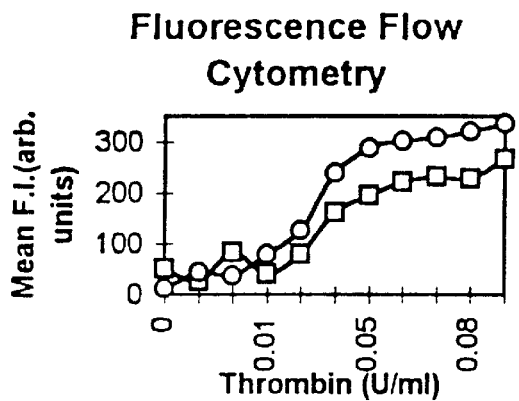
FIGS. 14A to 14D show a comparison between the novel light scattering method in accordance with the invention and a fluorescence method for determining platelet activation.
Figure 14C:
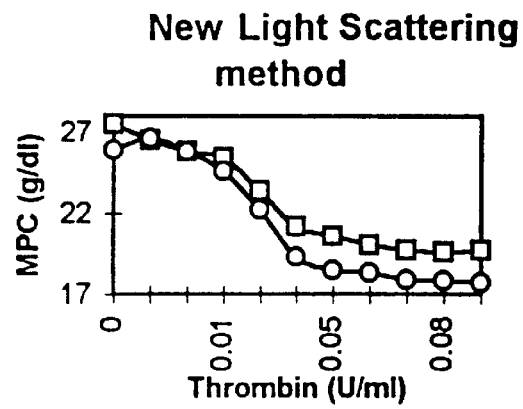
Figure 14B:
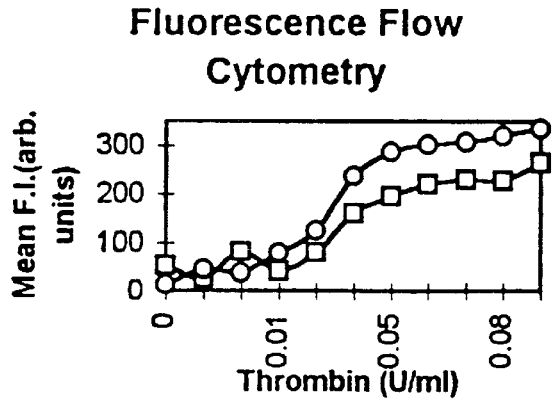
Figure 14D:
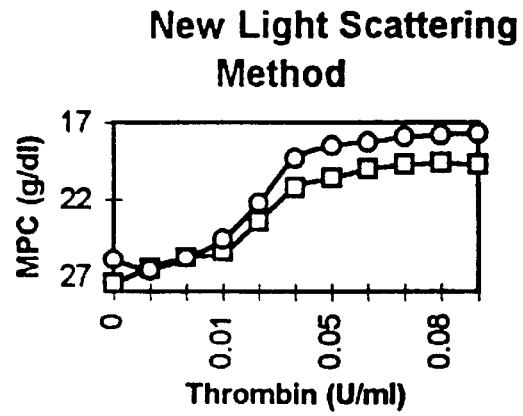

Although most of the abnormal samples described in Example 2 produced similar platelet counts regardless of the measurement method used, a small number of abnormal samples produced results that differed widely depending upon the analysis method. One such sample from a thrombocytopenic donor is described in this example. Table 8 presents the comparative platelet count data (samples were run in duplicate on the automated systems) and FIG. 13 displays the histograms produced by each of the three automated methods. As shown, only the PLT1 system of the invention produced platelet counts that agreed with the phase-contrast microscopy counts for both of the duplicate measurements. The TECHNICON H•™2 platelet counts were approximately double the phase contrast microscopy counts. The Coulter STKS System correctly reported the platelet count in only one of the duplicates, and blanked in the other. Also, the Coulter STKS and TECHNICON H•™2 volume histograms were not log-normal, because they included red blood cell fragment interference. Therefore, these two systems provided MPV values which were lower than the actual value, based on microscopic observation of the blood smear. The volume histogram generated by the PLT1 method and system was log-normal, and the reported MPV was within the range for thrombocytopenic samples and was also in qualitative agreement with microscopic observation. Further, platelet component concentration determined by the PLT1 system was roughly normally distributed and platelet dry mass was lognormally distributed, thus demonstrating that the particles which were counted as platelets in the abnormal samples by the present invention had the physical characteristics of platelets, as well.

TABLE 8

ABNORMAL THROMBOCYTOPENIC SAMPLE (DONOR #70)

| METHOD OF ANALYSIS | PLATELET COUNT (thousands/µl) |
|---|---|
| PHASE CONTRAST | 58 |
| PLT1 | 65/51 |
| TECHNICON H• ™2 | 102/90 |
| Coulter STKS | 65/— |

EXAMPLE 4

This example describes experiments performed to measure the dose response to in vitro platelet activation by thrombin. For these experiments, a blood sample was drawn from a normal adult human donor who was a non-smoker and was not undergoing aspirin therapy. Samples were collected both in sodium citrate and in $K_3$EDTA anticoagulants. A comparison of results based on the use of anticoagulants comprising $K_3$EDTA with those using sodium citrate demonstrates the utility of $K_3$EDTA for platelet activation studies employing the novel methods of the invention.

Thrombin-induced platelet activation was measured by fluorescence flow cytometric detection of an increased cell surface expression of an α-granule protein (GMP-140) using the phycoerythrin-conjugated monoclonal antibody, CD62-PE. The expression of GMP-140 is associated with α-granule release. This analysis is made possible by the inclusion of the tetrapeptide glycyl-L-prolyl-L-arginyl-L-proline (GPRP) described by Michelson et at., (A. D. Michelson et al. 1991, Blood, 77:770–779). GPRP inhibits platelet aggregation and fibrin clotting and therefore permits cell-by-cell analysis.

Sample Preparation

Whole blood was diluted 1:10 in PBS supplemented to contain 0.35% bovine serum albumin. Aliquots of diluted whole blood (300 µl) were incubated for 5 minutes in the presence of 2.5 mM GPRP (final concentration). α-thrombin was added to the test samples at final concentration of 0.002 U/ml to 0.087 U/ml as indicated in FIGS. 14A–D. PBS was added to the control samples. Samples were incubated for 15 minutes at room temperature and then were diluted 1:1 in 1% paraformaldehyde (in PBS) and incubated for 30 minutes at room temperature. Saturating concentrations of platelet-specific monoclonal antibodies directed against surface receptor GP1bIX (CD42a, FITC-conjugated and CD62-PE) were added to all samples analyzed by fluorescence flow cytometry, and the samples were incubated for 15 minutes. This step was omitted for samples analyzed by the method practiced in accordance with the invention. PBS was added to a final dilution of 1:600 before the samples were analyzed.

Sample Analysis

Samples were analyzed by a FACScan flow cytometer using a FACStation-CellQuest acquisition and analysis software (Becton Dickinson, San Jose, Calif.) equipped with an argon ion laser operating at 488 nm. The fluorescence of FITC and phycoerythrin were detected using 525 nm and 575 nm band pass filters, respectively. Platelets were identified by their forward scatter (FSC) versus side scatter (SSC) profile, as well as by FITC-positivity (green fluorescence, FL1). Activated platelets were identified by their PE-positivity (red fluorescence, FL2), i.e., FSC vs. FL2.

After the identification of platelets by light scatter gates and FITC-positivity, the binding of activation marker CD62 was determined by analyzing 5,000 platelet events for PE fluorescence. Background binding, measured using the isotypic antibody IgG, was subtracted from each sample. The results were reported as mean fluorescence intensity (FI, arbitrary units) for all samples. FI is more amenable to comparison with MPC than % positivity, since neither FI nor MPC required the setting of arbitrary thresholds. In addition, samples were analyzed by the absorption/light scatter method of the invention within two hours of collection.

The method of the invention and fluorescence flow cytometry methodology were compared by measuring platelet activation versus added thrombin (FIGS. 14A–14D). The results show that the light scattering method of the invention tracks thrombin dose-related platelet activation for blood samples anticoagulated with both sodium citrate (open circles) and $K_3$EDTA (open squares). As can be observed, with increasing concentrations of thrombin, the MPC decreases.

EXAMPLE 5

This example describes experiments performed to measure in vitro platelet auto-activation in $K_3$EDTA. For these experiments, a blood specimen was drawn from a normal adult human donor into $K_3$EDTA anticoagulant. Samples were prepared and analyzed as described for Example 4, but without thrombin activation and with paraformaldehyde added at the indicated times. Table 9 presents the results of the time course of platelet auto-activation in the presence of $K_3$EDTA.

TABLE 9

| Time of Sample Fixation After Collection (minutes) | FI (arbitrary units) | MPC (g/dl) |
| --- | --- | --- |
| 5 | 26 | 26.7 |
| 10 | 29 | 26.4 |
| 15 | 37 | 26.9 |
| 30 | 87 | 25.2 |
| 45 | 111 | 24.7 |
| 60 | 142 | 24.4 |

Table 9 shows that platelets in samples stored in EDTA undergo auto-activation which increases over time. Therefore, both fluorescence-based and light scattering-based measurements of platelet activation must account for in vitro sample age.

EXAMPLE 6

This example describes experiments performed to measure the activation state of platelets ex vivo. For these experiments, blood specimens were drawn from a normal human donor and from three diabetic donors. Samples were collected into $K_3$EDTA anticoagulant. Samples were prepared as described in Example 4 above, except that neither thrombin nor paraformaldehyde was added. Samples were analyzed 7 hours after collection. The results of these analyses are shown in Table 10.

TABLE 10

| Sample ID | FI (arbitrary units) | MPC (g/dl) |
| --- | --- | --- |
| Diabetic 1 | 426 | 21.1 |
| Diabetic 2 | 563 | 20.9 |
| Diabetic 3 | 81 | 24.2 |
| Normal | ND | 23.2 |

Table 10 indicates that both MPC and FI measurements distinguish between blood samples exhibiting platelet activation ex vivo (Diabetics 1 and 2) and those which do not (Diabetic 3). It can be observed that the FI is higher and the MPC is lower than expected, based on an examination of FIGS. 14A–14D. This suggests that all three of the diabetic samples are activated, but that the third sample is less activated than are the first two. MPC for a normal blood sample is also included to show that even for normal samples, MPC measured 7 hours after collection into EDTA solution is lower than for fresh samples. ND indicates not determined. The reason for the drop in MPC value and the rise in FI is that platelets stored in EDTA progressively auto-activate over time, as shown in Example 5 above. Nevertheless, MPC, as well as FI, distinguish between samples that experience in vivo platelet activation and those that do not.

The contents of all patent application, issued patents, published articles and references, and textbooks as cited herein are hereby incorporated by reference in their entirety to more fully describe the state of the art to which the present invention pertains.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

What is claimed is:

1. An automated method for accurately discriminating platelets from non-platelet particles or cells on a cell-by-cell basis in a normal or an abnormal whole blood sample and for determining qualitative and quantitative blood platelet parameters, comprising the steps of:

a) analyzing an aliquot of a suspension of said whole blood sample essentially one cell at a time through an aperture capable of detecting at least two measurable signals derivable from said non-platelet particles or cells and said platelets; wherein said measurable signals are detected within said aperture by at least one first detector and at least one second detector; wherein said at least one first detector is an optical detector comprising an optical channel capable of measuring scattered light intensity per unit scattering angle as a function of the scattering angle over a selected angle interval at an increased optical channel signal value, said optical channel signal value deriving from an increase in the gain of a high angle detector, said high angle detector capable of measuring said scattered light intensity over a high angle interval of approximately 5 to 20 degrees; and further wherein said first and second signal detectors produce amplified measurements of said signals sufficient to resolve platelets from non-platelets in said sample; and b) converting said signal measurements into corresponding platelet volume and refractive index values so as to resolve said platelets from said non-platelet particles or cells in said blood sample.

2. The method according to claim 1, wherein said second measurable signal is selected from the group consisting of light scatter, electrical impedance, light absorption and fluorescence.

3. The method according to claim 1, wherein said measurable signal detected by said second detector is electrical impedance.

4. The method according to claim 1, wherein said measurable signal detected by said second detector is fluorescence.

5. The method according to claim 1, wherein said measurable signal detected by said second detector is light scatter.

6. The method according to claim 5, wherein, in step a), said light scattering intensity is measured over two cone angle intervals in two optical channels at increased first and second optical channel signal values to produce two scattering intensity measurements sufficient to resolve platelets from non-platelets in said sample, wherein said first optical channel signal value derives from an increase in the gain of a high angle detector, said high angle detector capable of measuring said light scattering intensity over a high angle interval of approximately 5 to 20 degrees, and said second optical channel signal value derives from an increase in the gain of a low angle detector, said low angle detector capable of measuring said light scattering intensity over a low angle interval of approximately 1 to 7 degrees.

7. The method according to claim 6, wherein, in step b), said platelets are resolved from said non-platelets in said blood sample and platelet parameters are determined by the presence of light-scatter-derived platelet signals within a volume versus refractive index map.

8. The method according to claim 6, wherein said increase in said gain of said high angle detector is about 8 to 15-fold and said increase in said gain of said low angle detector is about 20 to 35-fold.

9. The method according to claim 8, wherein said increase in said gain of said high angle detector is about 12-fold and said increase in said gain of said low angle detector is about 30-fold.

10. The method according to claim 1, wherein said increase in said gain of said high angle detector is about 8 to 15-fold.

11. The method according to claim 10, wherein said increase in said gain of said high angle detector is about 12-fold.

12. The method according to claim 1, wherein the parameter of platelet count is determined, and further comprising the step of determining said platelet count based on particle volume and refractive index by placing said platelets within a volume versus refractive index map.

13. The method according to claim 12, wherein said platelets are identified as platelets based upon a normal distribution of the refractive indices of said platelets.

14. The method according to claim 1, wherein the parameters of platelet volume, platelet component concentration, and platelet dry mass are determined, and further comprising the steps of:
    c) converting said first and second signal measurements to a platelet volume value and a refractive index value of said platelets;
    d) converting said platelet refractive index value to a platelet component concentration value; and
    e) computing a platelet dry mass value as a product of said platelet component concentration value and said platelet volume value of steps c) and d).

15. The method according to claim 14, further comprising the step of
    f) displaying histograms of said platelet volumes, platelet component concentrations, and platelet dry masses.

16. The method according to claim 14, wherein said platelet component concentration value of said converting step d) is determined by subtracting the refractive index of water from the computed refractive index of the particle signals and dividing the result of said subtraction by an average refractive index increment.

17. The method according to claim 16, wherein said refractive index increment is 0.0018 g/dl.

18. The method according to claim 1, wherein said platelets are not perfectly sphered.

19. The method according to claim 1 or claim 6, wherein red blood cell counts are obtained by counting signals in high-gain channels X=99, Y=99 as red blood cells.

20. The method according to claim 19, wherein platelet analysis and red blood cell analysis are performed at the same time.

21. The method according to claim 6, wherein the volume and refractive index ranges are extended to avoid error due to saturation of said first and second optical channels by dense platelets having a size that is increased relative to that of normal platelets by extending downward the tables used under standard signal gain conditions to provide analyses of volume and refractive index of said platelets having increased size under normal gain conditions.

22. The method according to claim 1 or claim 14, wherein signal measurements obtained from said first and second detectors serve to determine the activation state of platelets, and wherein refractive index and mean platelet component concentration (MPC) values of activated platelets are measurably distinct from those of non-activated platelets.

23. The method according to claim 6, wherein said two light scattering measurements serve to determine the activation state of platelets, and wherein refractive index and mean platelet component concentration (MPC) values of activated platelets are measurably distinct from those of non-activated platelets.

24. The method according to claim 1, wherein said blood sample is mixed with an anticoagulant.

25. The method according to claim 24, wherein said anticoagulant is EDTA or sodium citrate.

26. The method according to claim 23, wherein said platelets are activated in vivo or ex vivo.

27. The method according to claim 23, wherein said activation state of platelets is a function of the in vitro age of a platelet sample.

28. The method according to claim 14, wherein said platelet component concentration value obtained in step d) determines the in vitro age of blood samples stored at from about one hour to about twenty-four hours at room temperature or at 4° C.

29. An automated process for accurately determining the parameters of platelet count, platelet volume, platelet dry mass, and platelet component concentration on a cell-by-cell basis and for discriminating platelets from non-platelet particles or cells in a normal or an abnormal whole blood sample, comprising the steps of:
    a) analyzing an aliquot of a suspension of said whole blood sample essentially one cell at a time through an aperture capable of detecting at least two measurable signals derivable from said non-platelet particles or cells and said platelets; wherein said measurable signals are detected within said aperture by at least one first detector and at least one second detector, wherein said at least one first detector is an optical detector comprising an optical channel capable of measuring scattered light intensity per unit scattering angle as a function of the scattering angle over a selected angle interval at an increased optical channel signal value, said optical channel signal value deriving from an increase in the gain of a high angle detector, said high angle detector capable of measuring said scattered light intensity over a high angle interval of approximately 5 to 20 degrees; and further wherein said first and second signal detectors produce amplified measurements of said signals sufficient to resolve platelets from non-platelets in said sample;
    b) converting said first and second detected signal values to a platelet volume value and a refractive index value of said platelets;
    c) converting said platelet refractive index value to a platelet component concentration value;
    d) computing a platelet dry mass value as a product of said platelet component concentration value and said platelet volume value of steps b) and c); and e) displaying histograms of said platelet volumes, platelet component concentrations, and platelet dry masses.

30. The process according to claim 29, wherein the parameter of platelet count is determined, and further comprising the step of determining said platelet count based on particle volume and refractive index by placing said platelets within said volume versus refractive index map.

31. The process according to claim 30, wherein said platelets are identified as platelets based upon a normal distribution of the refractive indices of said platelets.

32. The process according to claim 29, wherein, in step a), said increase in said high angle detector is about 8 to 15-fold.

33. The process according to claim 32, wherein, in step a), said increase in said high angle detector is about 12-fold.

34. The process according to claim 29, wherein said platelet component concentration value of said converting step c) is determined by subtracting the refractive index of water from the computed refractive index of the particle signals and dividing the result of said subtraction by an average refractive index increment.

35. The process according to claim 29, wherein said two detectable signal measurements serve to determine the activation state of platelets, and wherein refractive index and mean platelet component concentration (MPC) values of activated platelets are measurably distinct from those of non-activated platelets.

36. The process according to claim 35, wherein said activation state of platelets is a function of the in vitro age of a platelet sample.

37. An automated apparatus for accurately discriminating platelets from non-platelet particles or cells on a cell-by-cell basis in a normal or an abnormal whole blood sample and for determining qualitative and quantitative blood platelet parameters, comprising:

a) means for analyzing an aliquot of a suspension of said whole blood sample essentially one cell at a time through an aperture capable of detecting at least two measurable signals derivable from said non-platelet particles or cells and said platelets; wherein said measurable platelet and non-platelet signals are detected within said aperture by at least one first detector and at least one second detector; wherein said at least one first detector is an optical detector comprising an optical channel capable of measuring scattered light intensity per unit scattering angle as a function of the scattering angle over a selected angle interval at an increased optical channel signal value, said optical channel signal value deriving from an increase in the gain of a high angle detector, said high angle detector capable of measuring said scattered light intensity over a high angle interval of approximately 5 to 20 degrees;

b) means for resolving said platelets from said non-platelet particles or cells in said sample and determining said platelet parameters by placement within a volume versus refractive index map.

38. The apparatus according to claim 37, wherein said second measurable signal is selected from the group consisting of light scatter, electrical impedance, light absorption and fluorescence.

39. The apparatus according to claim 37, wherein said measurable signal detected by said second detector is electrical impedance.

40. The apparatus according to claim 37, wherein said measurable signal detected by said second detector is fluorescence.

41. The apparatus according to claim 37, wherein said measurable signal detected by said second detector is light scatter.

42. The apparatus according to claim 37, wherein, in said means for analyzing a), said light scattering intensity is measured over two cone angle intervals in two optical channels at increased first and second optical channel signal values to produce two scattering intensity measurements sufficient to resolve platelets from non-platelets in said sample, wherein said first optical channel signal value derives from an increase in the gain of a high angle detector, said high angle detector capable of measuring said light scattering intensity over a high angle interval of approximately 5 to 20 degrees, and said second optical channel signal value derives from an increase in the gain of a low angle detector, said low angle detector capable of measuring said light scattering intensity over a low angle interval of approximately 1 to 7 degrees.

43. The apparatus according to claim 42, wherein, in said means for resolving platelets b), said platelets are resolved from said non-platelets in said blood sample and platelet parameters are determined by the presence of light-scatter-derived platelet signals within a volume versus refractive index map.

44. The apparatus according to claim 42, wherein said increase in said gain of said high angle detector is about 8 to 15-fold and said increase in said gain of said low angle detector is about 20 to 35-fold.

45. The apparatus according to claim 44, wherein said increase in said gain of said high angle detector is about 12-fold and said increase in said gain of said low angle detector is about 30-fold.

46. The apparatus according to claim 37, wherein said increase in said gain of said high angle detector is about 8 to 15-fold.

47. The apparatus according to claim 46, wherein said increase in said gain of said high angle detector is about 12-fold.

48. The apparatus according to claim 37, wherein the parameter of platelet count is determined, and further comprising a means for determining said platelet count based on particle volume and refractive index by placing said platelets within a volume versus refractive index map.

49. The apparatus according to claim 37, wherein said platelets are identified as platelets based upon a normal distribution of the refractive indices of said platelets.

50. The apparatus according to claim 37, wherein the parameters of platelet volume, platelet component concentration, and platelet dry mass are determined, and further comprising:

c) means for converting said first and second signal measurements to a platelet volume value and a refractive index value of said platelets;

d) means for converting said platelet refractive index value to a platelet component concentration value; and e) means for computing a platelet dry mass value as a product of said platelet component concentration value and said platelet volume value of steps c) and d).

51. The apparatus according to claim 50, further comprising:

f) means for displaying histograms of said platelet volumes, platelet component concentrations, and platelet dry masses.

52. The apparatus according to claim 50, wherein said platelet component concentration value determined by said means for converting d) is determined by subtracting the refractive index of water from the computer refractive index of the particle signals and dividing the result of said subtraction by an average refractive index increment.

53. The apparatus according to claim 52, wherein said refractive index increment is 0.0018 g/dl.

54. The apparatus according to claim 37, wherein said platelets are not perfectly sphered.

55. The apparatus according to claim 37, further comprising means for obtaining red blood cell counts by counting signals in high-gain channels X=99, Y=99, as red blood cells.

56. The apparatus according to claim 55, further comprising means for performing platelet and red blood cell analyses at the same time.

57. The apparatus according to claim 42, further comprising means for extending said volume and refractive index ranges to avoid error due to saturation of said first and second optical channels by dense platelets having a size that is increased relative to that of normal platelets by extending downward the tables used under standard signal gain conditions to provide analyses of volume and refractive index of said platelets having increased size under normal gain conditions.

58. The apparatus according to claim 50, wherein said signal measurements obtained from said first and second detectors serve as means for determining the activation state of platelets, and wherein refractive index and mean platelet component concentration (MPC) values of activated platelets are measurably distinct from those of non-activated platelets.

59. The apparatus according to claim 58, wherein said platelets are mixed with an anticoagulant.

60. The apparatus according to claim 59, wherein said anticoagulant is EDTA or sodium citrate.

61. The apparatus according to claim 60, wherein said platelets are activated in vivo or ex vivo.

62. The apparatus according to claim 60, wherein said activation state of platelets is a function of the in vitro age of a platelet sample.

* * * * *